United States Patent
Quiachon et al.

[11] Patent Number: 5,938,623
[45] Date of Patent: Aug. 17, 1999

[54] GUIDE WIRE WITH ADJUSTABLE STIFFNESS

[75] Inventors: Dignah B. Quiachon, Mountain View; Robert A. Guziak, Pleasanton; Dennis L. Brooks, Windsor; Deepak R. Gandhi, San Jose; Mir A. Imran, Palo Alto; Roger J. Guidi, Los Altos, all of Calif.

[73] Assignee: Intella Interventional Systems, Sunnyvale, Calif.

[21] Appl. No.: 08/780,687

[22] Filed: Jan. 8, 1997

Related U.S. Application Data

[63] Continuation-in-part of application No. 08/690,749, Aug. 1, 1996, Pat. No. 5,813,997, which is a continuation of application No. 08/331,216, Oct. 28, 1994, Pat. No. 5,542,434, which is a continuation-in-part of application No. 08/585,855, Jan. 16, 1996.

[51] Int. Cl.[6] .................................................. A61B 5/00
[52] U.S. Cl. ............................................................. 600/585
[58] Field of Search .................................. 600/433–436, 600/585; 604/280–282

[56] References Cited

U.S. PATENT DOCUMENTS

| | | | |
|---|---|---|---|
| 5,052,404 | 10/1991 | Hodgson | 128/772 |
| 5,055,101 | 10/1991 | McCoy | 604/95 |
| 5,349,964 | 9/1994 | Imran et al. | 128/772 |
| 5,415,633 | 5/1995 | Lazarus et al. | 604/95 |
| 5,433,200 | 7/1995 | Fleischacker, Jr. | 128/657 |

*Primary Examiner*—Max Hindenburg
*Attorney, Agent, or Firm*—Flehr Hohbach Test Albritton & Herbert LLP

[57] ABSTRACT

Guide wire for use in a medical procedure and for use with a power supply comprising a solid core wire having proximal and distal extremities. The proximal extremity has a predetermined diameter. At least a portion of the distal extremity has a reduced size with respect to the predetermined diameter. A flexible coil is secured to the distal extremity of the core wire and extends over the portion of the core wire having a reduced size. An actuator member is disposed proximal of the coil and extends along the core wire. Electrical conductors extend from the proximal extremity of the core wire to the actuator member for supplying heat to the actuator member. The actuator member is formed of a temperature activated metal alloy having a Young's modulus of $4 \times 10^6$ to $14 \times 10^6$ psi which increases in stiffness when heat is supplied thereto to increase the stiffness of the guide wire proximally of the coil.

22 Claims, 8 Drawing Sheets

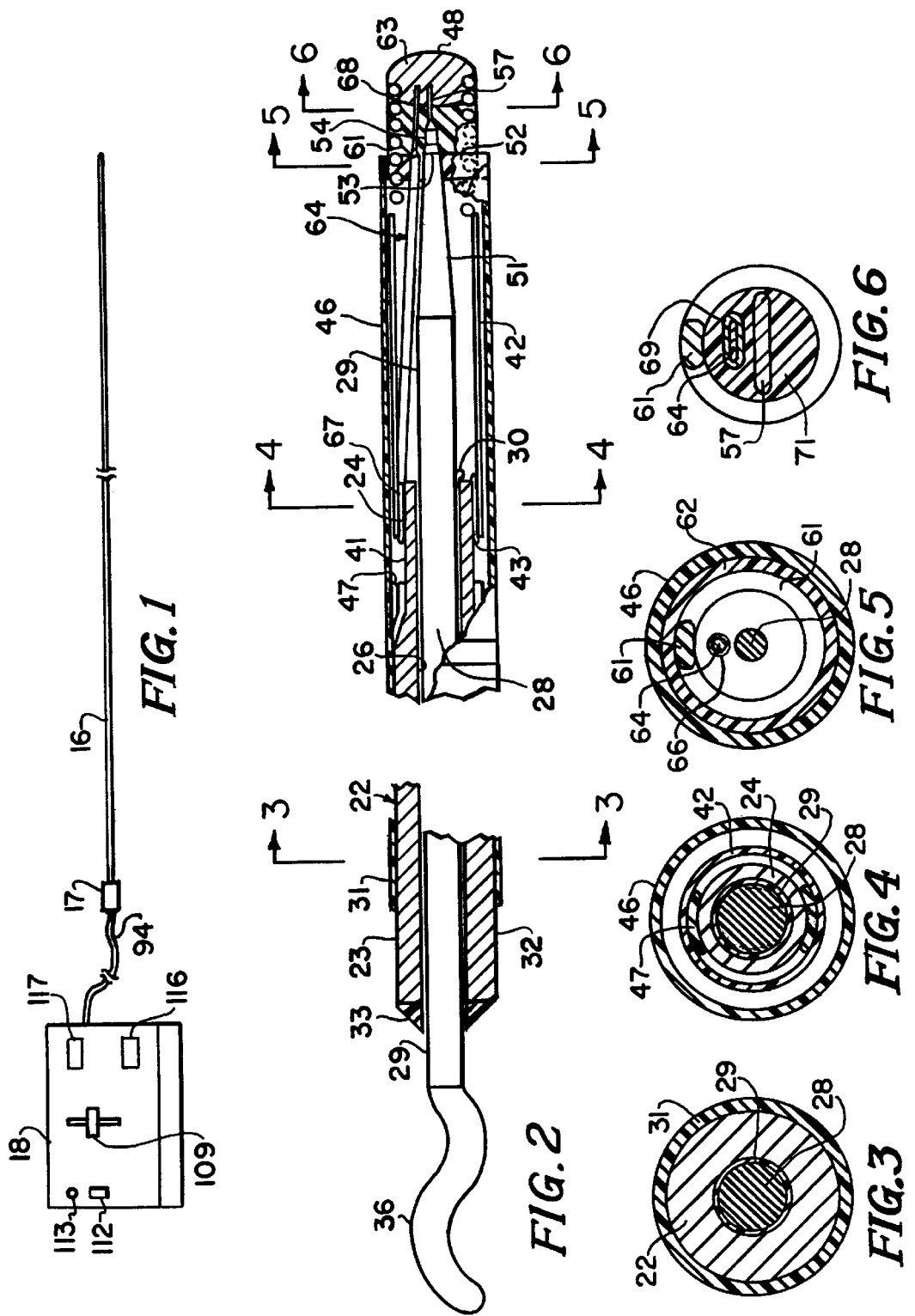

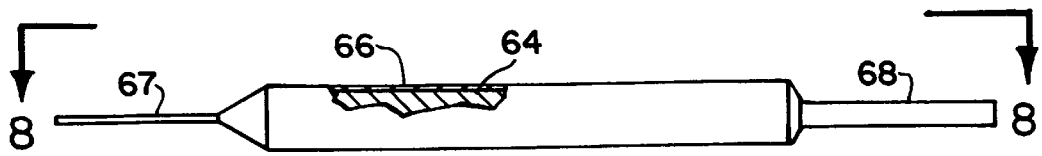
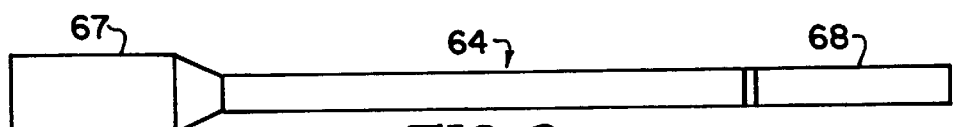
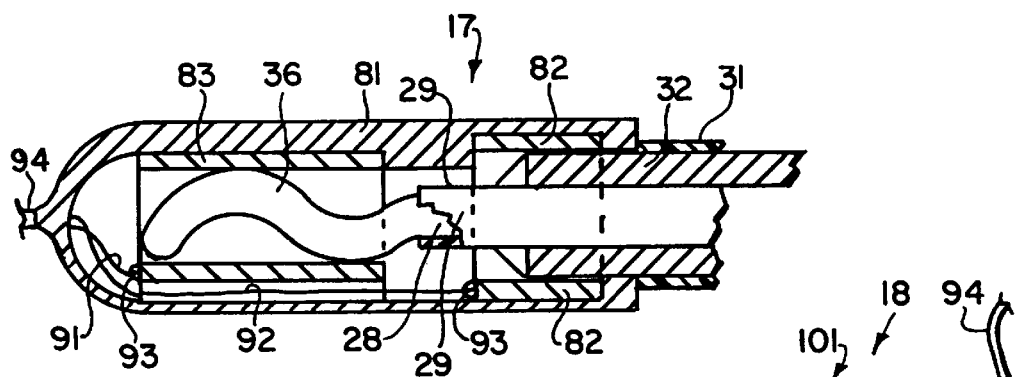
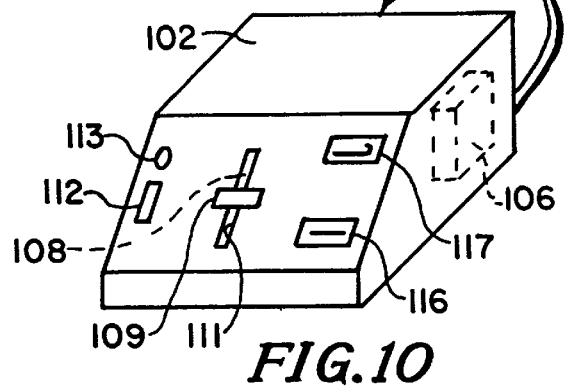
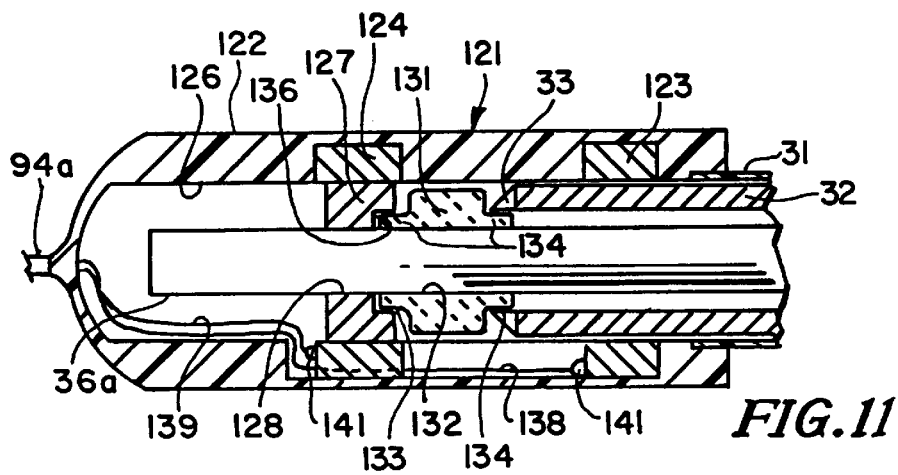

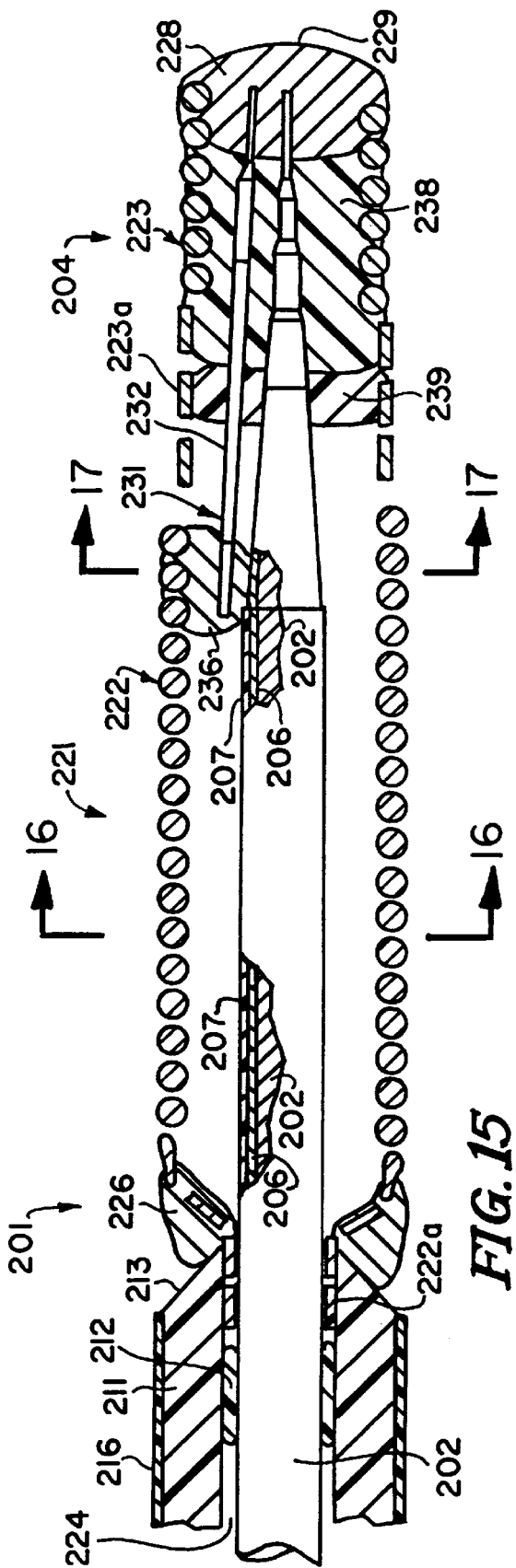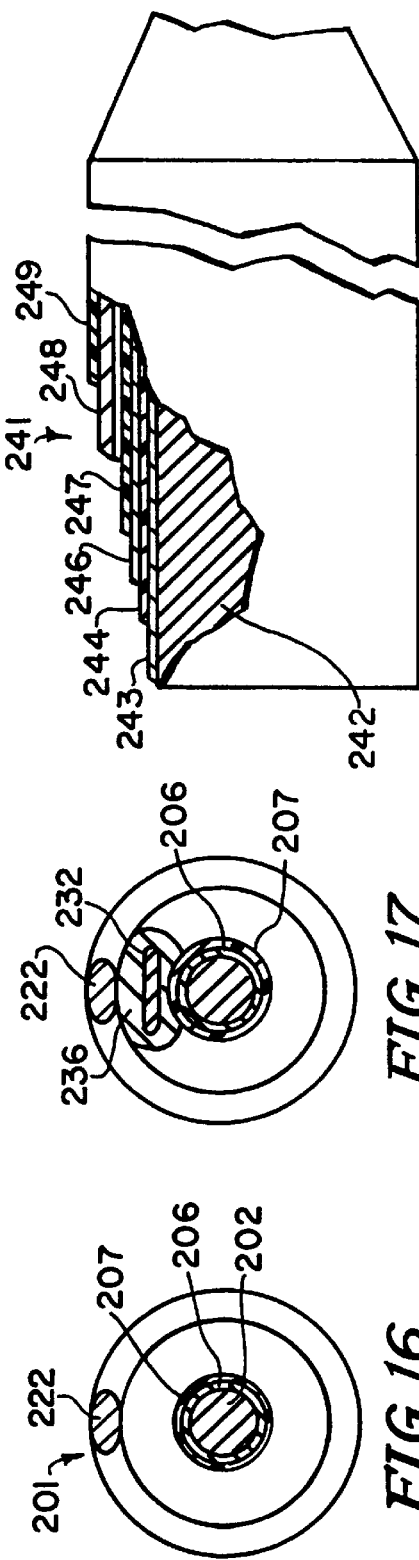

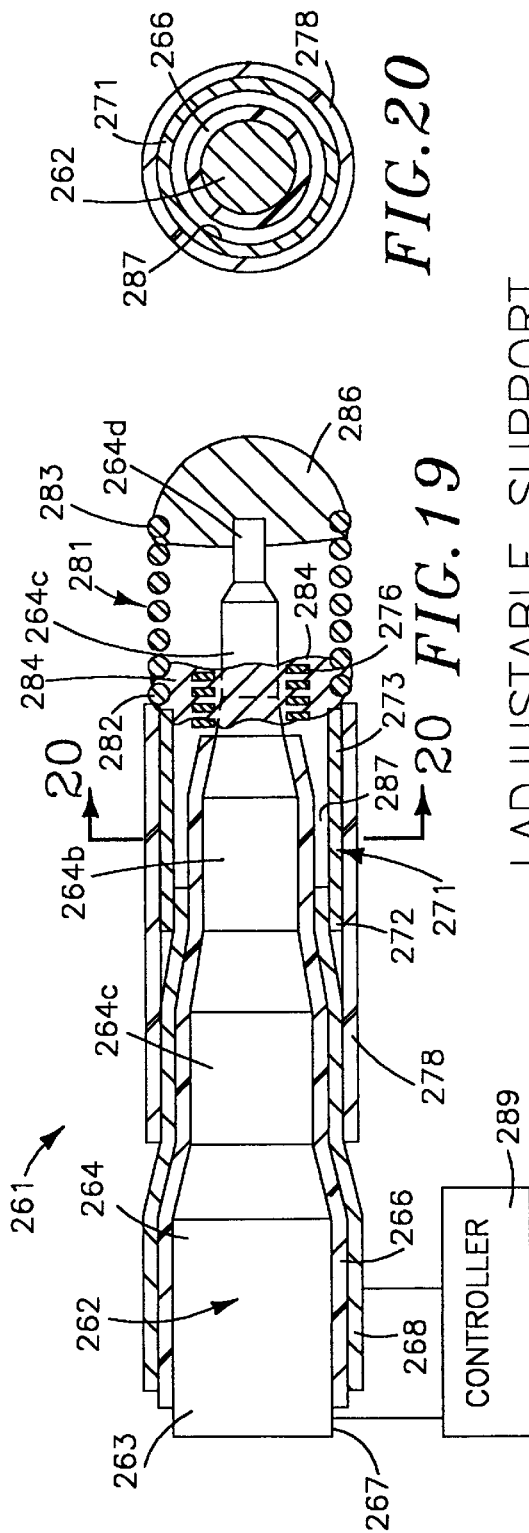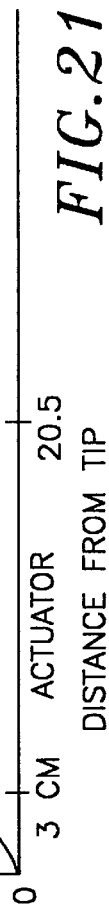

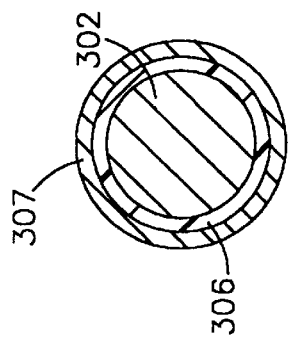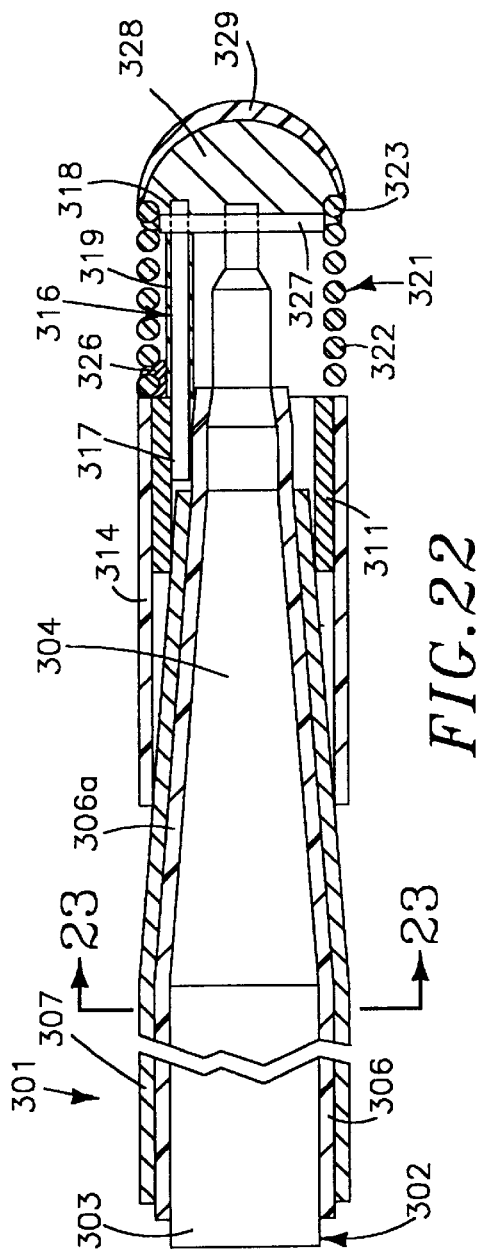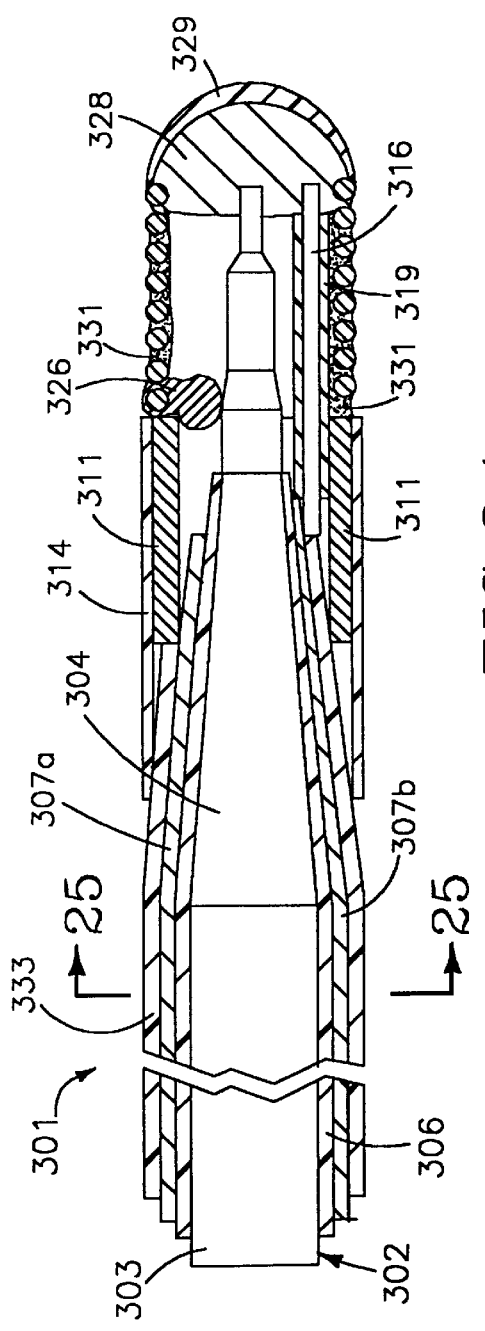

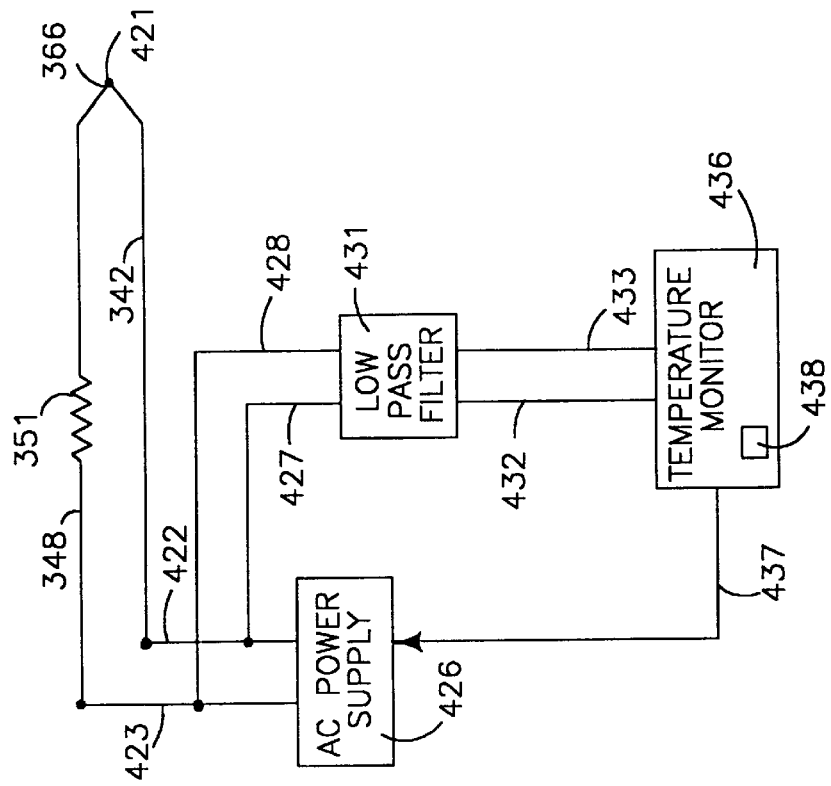
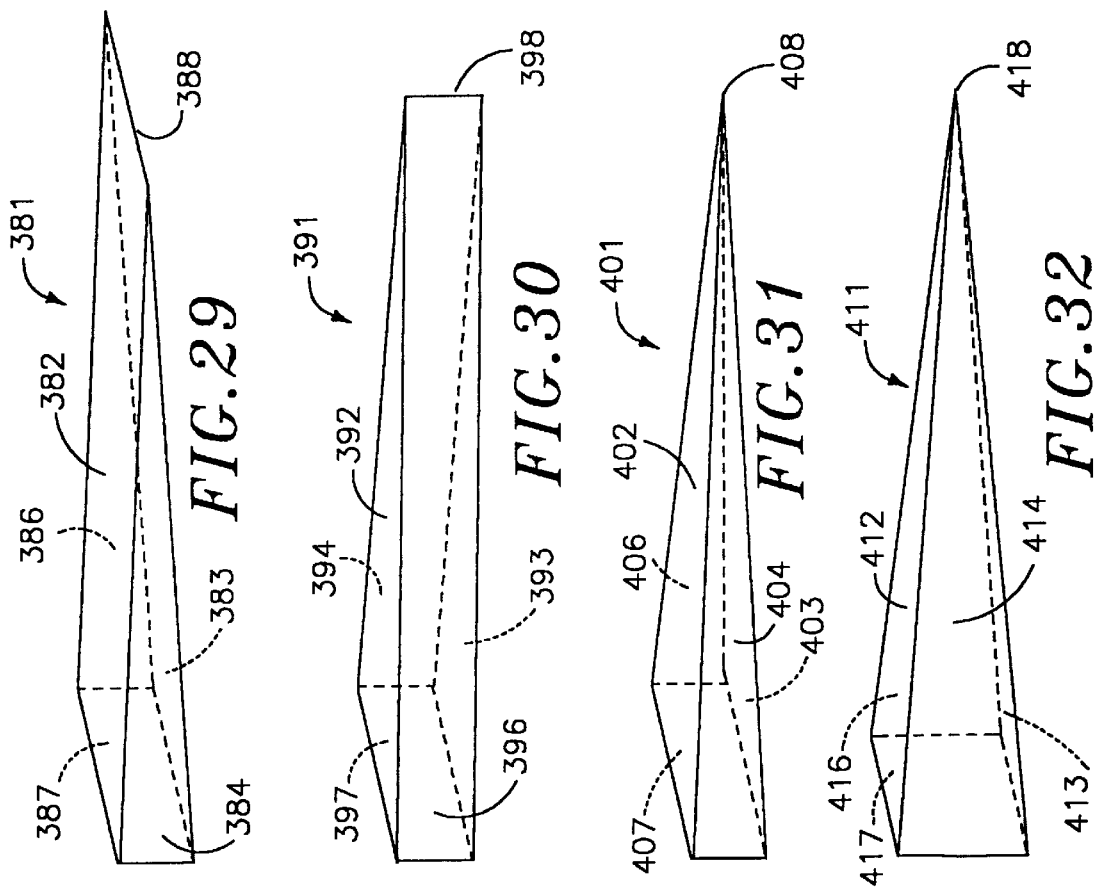

GUIDE WIRE WITH ADJUSTABLE STIFFNESS

This is a continuation-in-part of application Ser. No. 08/690,749 filed Aug. 1, 1996 now U.S. Pat. No. 5,813,997, which is a continuation of application Ser. No. 08/331,216 filed Oct. 28, 1994, now U.S. Pat. No. 5,542,434, which is a continuation-in-part of application Ser. No. 08/585,855 filed Jan. 6, 1996.

This invention relates to guide wires with adjustable stiffness and a method and more particularly to guide wires having adjustable stiffness tips and adjustable deflection guide wires having adjustable stiffness shaft portions for supporting stents.

Guide wires have been available in the past for many different applications including medical applications such as coronary angioplasty. In guide wires heretofore provided for angioplasty applications, such guide wires have been provided with flexible tips which typically can be shaped outside the body and then introduced into the body. With such a procedure it is often necessary to remove the guide wire from the body and reshape the distal extremity and reinsert the guide wire into the body to negotiate a tortuous vessel. Also, with such guide wires, the tips of the guide wires had insufficient stiffness to cross lesions which occlude or substantially occlude vessels. Guide wires for helping deliver stents have been provided with a stiffer distal extremity in order to achieve the stiffness required to place the stent in the desired location. When such a guide wire is provided with such stiffness, it is difficult to utilize such a guide wire for initially entering the vessel. This is true because with such guide wires it typically has been desirous that the tips be very floppy so that they can negotiate tortuosities encountered in the vessel. This often has made it necessary to utilize two guide wires in a single procedure, one guide wire being utilized having a floppy distal extremity for directing the guide wire into the desired location after which the floppy guide wire is removed and the other guide wire having a stiffer distal extremity being utilized for positioning a stent in the desired location. Therefore there is a need for a guide wire that does not have such limitations. Also, there is a need for providing a guide wire which can have a very floppy distal extremity and which can thereafter be made stiffer to aid in positioning a stent in the desired location.

In general, it is an object of the present invention to provide a guide wire which has an adjustable stiffness and method.

Another object of the invention is to provide a guide wire and method of the above character in which an adjustable stiffness is provided in the tip of the guide wire.

Another object of the invention is to provide a guide wire and method of the above character in which an adjustable stiffness is provided in a portion of the shaft of the guide wire to provide an adjustable support characteristic.

Another object of the invention is to provide a guide wire of the above character in which a sleeve of a superelastic material is provided at the distal extremity for adjusting stiffness.

Another object of the invention is to provide a guide wire of the above character which initially can have a very floppy distal extremity.

Another object of the invention is to provide a guide wire and method of the above character which can be utilized for deploying a stent.

Another object of the invention is to provide a guide wire of the above character which can be adjusted to provide additional support to aid in delivering a stent and which does not readily collapse or prolapse and does not resist placement of a stent delivery catheter.

Another object of the invention is to provide a guide wire and method of the above character which can be utilized with a balloon stent delivery catheter in which the guide wire provides strong mechanical support for deployment of the balloon and the stent.

Another object of the invention is to provide a guide wire and method of the above character in which additional stiffness can be imparted to the distal extremity to facilitate penetration of a stenosis in a vessel.

Another object of the present invention to provide a guide wire with a deflectable tip which can be deflected in vivo.

Another object of the invention is to provide a guide wire of the above character which can have diameters ranging from 0.010 inches to 0.038 inches and larger.

Another object of the invention is to provide a guide wire of the above character that can be relatively long in length.

Another object of the invention is to provide a guide wire and method of the above character in which different shapes can be provided in the distal extremity.

Another object of the invention is to include a guide wire and method of the above character in which the different predetermined shapes can be incorporated into the tip.

Another object of the invention is to provide a guide wire and method of the above character in which the distal extremity can be provided with a pre-bend before insertion into the vessel.

Another object of the invention is to provide a guide wire and method of the above character in which localized heating is utilized to minimize the introduction of heat into the bloodstream in the vessel.

Another object of the invention is to provide a guide wire and method of the above character in which various degrees of floppiness can be achieved in the distal extremity.

Another object of the invention is to provide a guide wire and method of the above character in which the tip can be deflected in substantially real time.

Another object of the invention is to provide a guide wire and method of the above character in which coaxial conductors are utilized to maximize the size of the coil wire, to reduce any tendency to whip and to facilitate manufacture.

Additional objects and features of the invention will appear from the following description in which the preferred embodiments are set forth in detail in conjunction with the accompanying drawings.

FIG. 1 is a side-elevational view of guide wire having a deflectable tip with a control console incorporating the present invention.

FIG. 2 is an enlarged view of partially in section of the guide wire, shown in FIG. 1.

FIG. 3 is a cross sectioned view taken along the line 3—3 of FIG. 2.

FIG. 4 is a cross-sectional view taken along the line 4—4 of FIG. 2.

FIG. 5 is a cross-sectional view taken along the line 5—5 of FIG. 2.

FIG. 6 is a cross-sectional view taken along the line 6—6 of FIG. 2.

FIG. 7 is a side-elevational view of the actuator wire utilized in the guide wire shown in FIG. 1.

FIG. 8 is a plan view of the actuator wire shown in FIG. 7 looking along the line 8—8 of FIG. 7.

FIG. 9 is a side-elevational view partially in section of the connector used with the guide wire shown in FIGS. 1 through 6.

FIG. 10 is an enlarged isometric view of the control console shown in FIGS. 1 through 9.

FIG. 11 is a partial side-elevational view partially in section of another embodiment of a guide wire incorporating the present invention utilizing an alternative connector.

FIG. 15 is a side-elevational view partially in section of the distal extremity of another embodiment of a guide wire incorporating the present invention.

FIG. 16 is a cross-sectional view taken along the line 16—16 of FIG. 15.

FIG. 17 is a cross-sectional view taken along the line 17—17 of FIG. 15.

FIG. 18 is a partial side-elevational view partially in section of another embodiment of the guide wire incorporating the present invention.

FIG. 19 is a sectional view of another embodiment of a guide wire incorporating the present invention in which additional stiffness can be imparted to a shaft portion of the guide wire.

FIG. 20 is a cross-sectional view taken along the line 20—20 of FIG. 19.

FIG. 21 is a graph showing the support provided in the shaft portion of the guide wire and showing the change in support provided between activated and non-activated states.

FIG. 22 is a sectional view of still another embodiment of the guide wire incorporating the present invention in which additional stiffness can be imparted to a shaft portion of the guide wire.

FIG. 23 is a cross-sectional view taken along the line 23—23 of FIG. 21.

FIG. 24 is a sectional view of another embodiment of a guide wire incorporating the present invention taken along the line 24—24 of FIG. 25.

FIG. 25 is a cross-sectional view taken along the line 25—25 of FIG. 24.

FIGS. 29–32 are isometric views of additional embodiments of actuators incorporating the present invention which can be utilized in the guide wire shown in FIGS. 26 and 27.

FIG. 33 is a schematic block diagram showing circuitry which can be utilized with the guide wires of the present invention for calibrating the guide wire.

Figure 12:
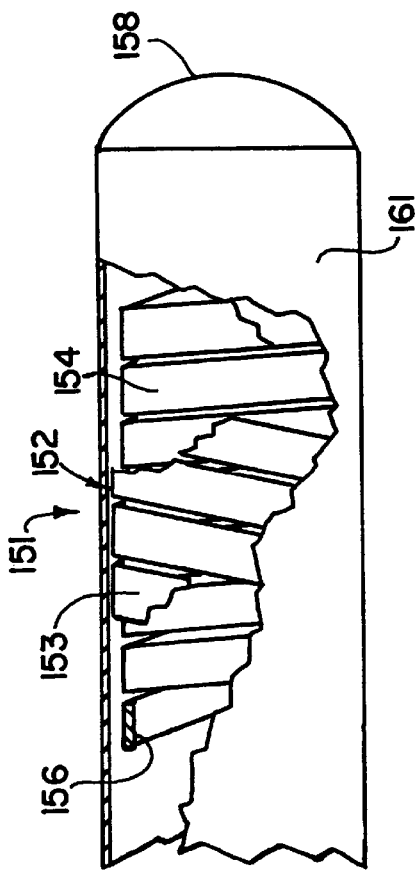
FIG. 12 is an isometric side-elevational view partially in section of another embodiment of a guide wire incorporating the present invention.

In general, the guide wire of the present invention is for use in a medical procedure and for use with a power supply comprising a solid core wire having proximal and distal extremities, the proximal extremity having a predetermined diameter, at least a portion of the distal extremity having a reduced size with respect to the predetermined diameter, a flexible coil secured to the distal extremity of the core wire and extending over the portion of the core wire having a reduced size, an actuator member disposed proximal of the coil and extending along the core wire, electrical conductive means extending from the proximal extremity of the core wire and to the actuator member for supplying heat to the actuator member, said actuator member being formed of a temperature activated metal alloy having a Young's modulus of $4 \times 10^6$ to $14 \times 10^6$ psi which increases in stiffness when heat is supplied thereto to increase the stiffness of the guide wire proximally of the coil.

More particularly as shown in FIGS. 1–10, the guide wire 16 shown therein is of the type which is particularly adapted for coronary and cardiology applications. It is connected to a connector assembly 17 connected to a control console 18. The guide wire 16 consists of a flexible elongate tubular member 22 having proximal and distal extremities 23 and 24. The flexible elongate tubular member 22 can be formed of a suitable material such as stainless steel, having a suitable outside diameter, as for example 0.013 inches and a wall thickness ranging from 0.0015" to 0.0035". The guide wire 16 can have a suitable length as for example 175 to 180 cms with the flexible elongate tubular member 22 in such an embodiment having a suitable length as for example 150 cms. The flexible elongate tubular member 22 is provided with a bore 26 of a suitable diameter as for example 0.009" to 0.010" extending from the proximal extremity 23 to the distal extremity 24. The hypotube in the present embodiment has an inside diameter of approximately 0.006" to 0.018" and preferably 0.010" which would mean that the 0.0014" outside diameter hypo tube would have a nominal wall thickness of 0.002".

An inner mandrel or core wire 28 also formed of a suitable material such as stainless steel and having suitable diameter as for example 0.006" is disposed in the bore 26 and extends the length thereof. Generally it is desirable that the inner mandrel or core wire 28 have as large a diameter as possible. Thus with a 0.013" flexible elongate tubular member 22, a core wire can have an outside diameter ranging up to 0.0075" to 0.008" to provide improved torque characteristics. It should be appreciated that the inner mandrel or core wire 28 can be formed of other hybrid materials such as Nitinol and other alloys. The mandrel or core wire 28 tip is heat treated and annealed to prevent whipping of the guide wire 16 as the guide wire 16 is rotated. The outside surface of the core wire 28 is coated with a suitable insulating material as for example a thin wall polyimide coating 29 having a thickness ranging from 0.00025" to 0.0005". This polyimide coating 29 extends the length of the core wire 28 and serves to insulate the core wire 28 from the flexible elongate tubular member 22. The distal extremity 24 of the flexible elongate tubular member 22 is bonded to the core wire 28 by an adhesive 30.

An insulation layer 31 is also provided on the outside surface of the flexible elongate tubular member 22 which can be formed of a suitable material such as polyethylene, polyimide or PET and having a thickness range from 0.0002 to 0.0008". The proximal extremity of the flexible elongate tubular member 22 is not covered by the insulating layer 31 and serves as a sleeve 32 for making electrical contact to the sleeve as hereinafter described. A fillet 33 formed of a suitable adhesive such as a polyurethane provides a transition between the flexible elongate tubular member 22, or in other words a stainless steel hypo tube 22 to the polyimide coating or insulation 29 provided on the core wire 28. It should be appreciated that in place of the adhesive fillet 33, a piece of plastic shrink tubing could be used to make the transition from the stainless steel hypo tube or flexible elongate member 22 to the core wire 28 to provide the desired graduated transition between the same. The proximal extremity of the inner mandrel core wire 28 is not covered with the insulating coating or layer 29 and is crimped or coined to provide an end 36 which can serve as an exchange wire as hereinafter described.

The construction of the guide wire 16 from the cross sections shown in FIG. 3 and FIG. 4 show that the construction is substantially identical from the proximal extremity of the guide wire shown in FIG. 3 to the distal extremity of the flexible elongate tubular member 22 near to the cross section of FIG. 4. As shown in FIG. 2, the distal extremity of the flexible elongate tubular member 22 is tapered to provide a conical portion 41 to reduce outside diameter of the flexible elongate tubular member from about 0.014" to about 0.007". An inner insulating sleeve 42 of a suitable insulating material such as a polyimide has a proximal extremity secured to the distal extremity of the flexible elongate tubular member 22 distal of the taper 41 by suitable means such as an adhesive 43. An outer sleeve 46 of the same or similar insulating material has its proximal extremity secured to the taper 41 of the flexible elongate tubular member 22 with the insulating layer 31 thereon by a suitable means such as an adhesive 47. The insulating layer sleeve 31 extends from the proximal extremity of the flexible elongate tubular member 22 and then extends over the inwardly extending taper 41 and underlies the proximal extremity of the outer insulating sleeve 46 formed of a suitable material such as a polyimide. The inner and outer sleeves 42 and 46 can have suitable outside diameters, for example the inner sleeve can have an outside diameter ranging from 0.008" to 0.014" whereas the sleeve 46 can have an outside range from 0.010" to 0.018".

It should be appreciated that the outer insulating sleeve 31 can possibly be eliminated in certain applications. Although in the present construction it does serve to provide some additional insulation and it also serves to protect the flexible elongate tubular member 22 from the blood or other fluid into which the guide wire is inserted. It also should be appreciated that if desired a single shrink tube of insulating material could be substituted for the outer sleeve 46 and the inner sleeve 31 in certain applications.

The flexible elongate tubular member 22 terminates at a distance of approximately 15 to 30 cms from a tip 48 of the guide wire. The core wire 28 extends out of the distal extremity 24 of the flexible elongate tubular member 22 and is of a uniform diameter of approximately 0.008" until approximately 8–12 cms from the tip 48 where it is provided with a centerless ground taper 51 for a distance of 3–5 cm. This is followed by another taper 53 reducing the diameter from 0.0024" to a flat 54 having a thickness of 0.002" and a width of 0.004" and having a length of approximately 1 cm. This is followed by another taper 56 to another flat 57 having a length of approximately 1 cm and having a thickness of 0.001" and a width of 0.006". The flats 54 and 57 provide preferential bending in one direction as hereinafter described.

A coil 61 formed of a suitable radiopaque material such as a platinum-tungsten or platinum-irridium alloy is secured within the distal extremity of the polyimide outer sleeve 46 by suitable means such as an adhesive 62. The coil 61 is secured in such a manner so that its proximal extremity abuts the distal extremity of the inner insulating sleeve 42. By way of example the coil 61 can be formed of a wire material having a diameter of 0.025" which is wound into a coil having a diameter of 0.0125" and a suitable length as for example 3.5 cms. A weld 63 formed as a round globule can be in the form of a radiopaque solder that adheres to the distal extremity of the coil 61 and has embedded therein the distal extremities of the flat 57 of the core wire 28.

Means is provided for causing bending of the distal extremity of the guide wire 16 and consists of an actuator wire 64 formed of a suitable shape memory material such as Nitinol. It is desirable that this shape memory material make a transformation from martensite to austenite between 45 and 60° C. It is desirable that it be a temperature which is above the body temperature of 37° C. but be at a temperature below 70° C. so as to reduce the amount of current required to cause transformation from the martensitic to austenitic phase. The actuator wire 64 should be formed of a nickel titanium alloy which has a narrow hystereses loop. This is desirable because when the wire returns to its martensitic state the guide wire should reach this condition at a temperature above body temperature. The overall length of the pull or actuator wire 64 can range from 1 cm to 40 cms in the present embodiment with a preferable length of 17 cms.

The actuator wire 64 is provided with a conductive plating or coating 66 (see FIGS. 5 and 7) formed of a suitable material such as silver having a suitable thickness as for example 0.0002" extending the entire length of the flattened proximal and distal extremities 67 and 68 as shown in FIG. 7. The proximal extremity 67 is bonded to the distal extremity or taper 41 of the hypotube 22 by suitable means such as a silver epoxy (not shown). The conductive coating 66 is covered with a coating 69 of a suitable insulating material such as a polyimide having a suitable thickness as for example 0.0002". The polyimide coating 69 does not extend over the proximal portion 67 of the actuator wire 64 but does extend near the distal extremity 68 (see FIG. 6).

The silver coating 66 is provided to reduce the resistance of the actuator wire 64 to thereby reduce the power that is necessary to cause deflection of the actuator wire. When the current reaches the unplated distal extremity 68 of the actuator wire 64 the unplated or recoated distal extremity has a higher resistance because of the absence of the plating which causes bending of the distal extremity of the actuator wire 64. Thus with such a construction it is seen that only a minimum amount of heating is imparted to the distal extremity of the guide wire and that this heating is only that required for causing bending of the distal most extremity 68 in accordance with the shape memory which has been placed therein. The shape memory incorporated into the distal extremity 68 can be one which when the distal extremity is heated it will become curved as for example to form a 90° bend or greater or alternatively when heated will assume a straight shape. If the actuator wire 64 is to form a bend standing through more than 90° as for example up to 180° the distal extremity of the guide wire 16 will have a hook-like appearance which typically should not have a diameter which exceeds 2 centimeters. With such a shape memory actuator wire 64, the distal extremity of the guide wire 16 will be normally straight and will only become shaped or take a radius of curvature when the actuator wire 16 is heated to activate the memory which has been placed in the actuator wire 64.

In order to further inhibit the transfer of energy into the blood in which the tip 48 of the guide wire may be immersed, a coating 71 such as silicon fills the space in the coil 61 between the weld 63 and the adhesive 62.

In the embodiment of the actuator wire 64 hereinbefore described and shown in FIGS. 2–8, the actuator wire has a diameter of 0.0025". This diameter however can range from 0.001" to 0.005". The proximal end 67 shown in FIGS. 7 and 8 can be flattened so it has a thickness of approximately 0.001" and having the width of approximately 0.005" and having a length ranging from 1 to 2 cms. The distal extremity 68 also has been flattened to a thickness of approximately 0.0015" and can have the same width ranging from 0.002" to 0.004". It can have a length ranging from 1-½ to 3 cms. It should be appreciated that the actuator wire 64 can have a rectangular cross section along its entire length to form a ribbon as for example a width of 0.004" to 0.006" and a thickness of 0.0015" to 0.002".

The connector 17 as shown particularly in FIG. 9 consists of a housing 81 formed of a suitable material such as plastic which carries first and second spaced apart conductive sleeves or rings 82 and 83 formed of a suitable material such as beryllium copper. Ring 82 engages and forms a part of the sleeve 32 carried by the flexible elongate tubular member 22. Sleeve 83 is adapted to engage the coined end 36 of the core wire 29. Insulated conductors 91 and 92 formed of a suitable conductive material such as copper are connected by a suitable means such as solder 93 to the rings 82 and 83 and are connected into a cable 94 which is connected to the control console 18. The connector 17 is sized to make a friction fit with the coined end 36 on the proximal extremity 23 of the guide wire 16 so that it can be installed and removed with a small amount of force as for example, 50 to 70 grams. The frictional retaining force should be sufficient to retain the connector 17 connected to the guide wire 16 and not accidentally fall off.

The control console 18 as shown more specifically in FIG. 10 consists of a housing 101 which is provided with an inclined front panel 102 (see FIG. 10). The housing 101 is provided with an output connector (not shown) which is adapted to receive the cable 94. The housing 101 houses a suitable power supply as for example a battery pack 106. The battery pack 106 is connected to circuitry (not shown) which can be of a conventional type for supplying the power from the battery to a linear potentiometer 108 which has a slider (not shown) connected to a handle 109 that extends through a slot 111 extending upwardly and downwardly of the front panel 102 to control the amount of power supplied to the actuator wire 64. An on/off switch 112 is also mounted on the front panel 102 and a light 113 is mounted on the front panel 102 in the vicinity thereof to indicate when power is on or off. Graphic displays 116 and 117 are provided on the front panel for representing tip deflection with display 117 showing a 90° deflection and display 116 showing a 0° deflection.

Operation and use of such guide wire may now be briefly described as follows. Let it be assumed that it is desired to utilize the guide wire 16 in a conventional angioplasty procedure. The physician removes the guide wire 16 from the package in which it was shipped. Let it be assumed that the guide wire 16 has been provided with a shape memory which assumes a bend upon being heated but otherwise will be straight. However, the distal extremity of the guide wire 16 will be very soft to provide an atraumatic floppy tip which is nearly equivalent to the stiffness i.e., or floppiness of a conventional ACS High Torque™ floppy guide wire. The guide wire 16 can be advanced into a guiding catheter which has already been placed in a vessel of the patient and then advanced into the coronary vessel in which it is desired to obtain access to a stenosis in a coronary vessel.

It should be appreciated that the guide wire 16 can be provided with a torquer of a conventional type to aid in torquing the guide wire 16 during the time it is being advanced into the vessel of the patient. In connection with the present procedure, the guide wire can first be advanced to the desired location and then the angioplasty or balloon catheter advanced over the guide wire to the desired position in the stenosis or alternatively, if desired, a balloon catheter can be preloaded onto the guide wire 16 with the distal extremity of the guide wire 16 extending beyond the catheter. With the entire procedure being viewed fluoroscopically, let it be assumed that the physician reaches a bifurcation in a coronary vessel and that it is desired to advance into a particular branch to reach a stenosis that can only be accomplished by forming a curve in the distal extremity of the guide wire 16. As soon as the physician ascertains that this is necessary, the physician merely grasps the handle 109 of the linear potentiometer 108 to supply power to the actuator wire 64. As pointed out previously, the current will flow through the low resistance silver coating 66 into the high resistance distal extremity 68 of the actuator wire 64 to cause heating of the distal extremity 68 to cause it to reach a temperature to cause the material to transfer from a martensitic state to an austenitic state and to thereby cause the tip of the guide wire 16 to begin to bend. As soon as the deflection or bending of the amount desired has occurred by observing the distal extremity fluoroscopically and also viewing the display 117, the physician can advance the guide wire 16 into the desired branch vessel. Because of the low mass of the material, the response time for the bending of the distal extremity of the guide wire 16 is very short, i.e., approximately 1 to 2 seconds, so that movement of the tip 48 of the guide wire 16 in response to movement of the handle 109 is substantially in real time. This makes it possible for the physician to establish the desired bend in the distal extremity of the guide wire 16 while it is "on the fly". Thus it is possible for a physician operating the slide control handle 109 of the linear potentiometer 108 to cause the distal extremity of the guide wire 16 to advance through a tortuous vessel by repeated heating and cooling of the actuator wire 64 under the control of the handle 109. When the handle 109 has been returned to a home position the distal extremity of the guide wire 16 is straight and can be advanced through a stenosis. Thereafter a conventional balloon catheter is advanced over the guide wire 16 to position the balloon in the stenosis to perform an angioplasty in a conventional manner.

Since the distal extremity 68 of the actuator wire 64 lies in a plane, the bending hereinbefore described will also occur in the plane of the distal extremity 68. Bending in this plane can extend from 0° to 90° and even to 180° and greater if desired by providing such a preformed memory in the actuator.

With the guide wire 16 of the present invention, it is possible to provide a guide wire which has a very floppy atraumatic tip that corresponds in characteristics very similar to the floppiness of a conventional high torque floppy guide wire. However, when the actuator wire 64 is energized it will become slightly stiffer so that its stiffness is between that of a conventional high torque floppy guide wire and a conventional intermediate guide wire.

By providing such a guide wire 16 having a bendable distal extremity which can be controlled from a remote location as for example at the control console 18, it is possible to negotiate a vessel with a single pass of the guide wire 16. It is unnecessary to pull out the guide wire and reconfigure the tip as has been done in the past with respect to the high torque floppy guide wires. This greatly reduces the time required to advance the distal extremity of a guide wire into the desired location reducing the amount of time required by the physician and also decreasing the amount of X-ray exposure to the patient during fluoroscopy. Thus the time required for the entire medical procedure is reduced. The bending of the distal extremity can be accomplished by use of very small amounts of energy as for example 1 to 200 milliamperes for very small amounts of time i.e., 1 to 2 seconds, thereby minimizing the amount of heat which is supplied to the distal extremity of the guide wire and into the blood in the vessel being negotiated. Only enough current is supplied to heat the distal extremity 68 so that very little heat is imparted to the other portions of the distal extremity of the guide wires 16. The response time is less than 2 seconds in achieving a bend ranging from any degree beyond 0° through 180° and even greater if desired. By reducing the amount of heating desired, the amount of heat that is supplied to the blood in the bloodstream passing through the vessel is minimized. This localized heating of the actuator wire 64 makes this possible.

In FIG. 11, there is shown a connector 122 which can be utilized in connection with a guide wire of the type which does not have a crimped or coined end 36 as shown in FIG. 2 but which has a straight end identified as 36a in FIG. 11. As can be seen in FIG. 11, the end 36a is cylindrical or straight. The connector 122 consists of a housing 133 formed of a suitable material such as plastic. First and second spaced-apart slip rings 123 and 124 formed of a suitable material such as beryllium copper are carried by the housing 133. The slip rings 123 and 124 extend into a cylindrical bore 126 provided in the housing 133. The slip ring 123 is adapted to frictionally engage the sleeve 32 provided on the proximal extremity 23 of the flexible elongate member 22. The slip ring 124 is adapted to frictionally engage a contact ring 127 also formed of a suitable material such as beryllium copper. The contact ring 127 is provided with a bore 128 which is sized so that the contact ring 127 frictionally engages the core wire 36a and is retained thereon. A cylindrical spacer 131 formed of a suitable insulating material such as plastic or a ceramic is similarly provided with a bore 132 that is sized so that the spacer 131 frictionally engages the core wire 36a. If desired the spacer 131 can be retained on the core wire 36a by suitable means such as an adhesive.

As shown in FIG. 11 to provide additional frictional engagement with the core wire tip 36a, the spacer 131 can be provided with annular lips 134 extending axially therefrom with the annular lip 134 underlying the fillet 33 and with the annular lip 134 being seated within annular recess 136 provided in the contact ring 127. Insulated conductors 138 and 139 are secured to the rings 123 and 124 by solder 141 and are connected into the cable 94a which is connected to the control console 18.

If an exchange wire is utilized with a core wire of the type of core wire 36a, the extension wire can be provided with the similar construction as the connector 122. Alternatively, the contact ring 127 and the spacer 131 can be removed from the proximal extremity of the core wire 36a.

In a modified embodiment of the guide wire 16 shown in FIG. 2, the actuator wire 64 can have a greater diameter as for example a diameter of 0.003" versus the 0.0025" hereinbefore described in conjunction with the guide wire 16. This larger diameter actuator wire 64 provides a greater force to overcome the predetermined set which may be placed in the distal extremity or flat 57 of the core wire 28. As explained previously, the core wire 64 can be formed of a suitable material such as nickel titanium alloy or stainless steel which can be provided with a predetermined shape set or can be bent by the physician in the desired manner prior to insertion of the guide wire into the vessel of the patient. This makes it possible for the physician to preshape the coil spring 61 provided on the distal extremity of the guide wire. Alternatively, the coil spring 61 can be preset to a particular shape as for example a bend of 45° or 90°. With such an embodiment of the guide wire 16, it is possible for the physician to use a preset curve and then to advance the distal extremity of the guide wire into the vicinity of the stenosis. Thereafter, the control handle 109 can be operated to supply energy to the actuator wire 64 to cause it to stiffen and assume a straight shape in accordance with the shape memory incorporated therein. The stiff or straight tip of the guide wire 16 can then be advanced through the stenosis.

By increasing the stiffness of the tip by increasing the current flow, the column strength of the distal extremity of the guide wire 16 is increased to make it possible to traverse the stenosis even though the stenosis may occlude or almost completely occlude the vessel. Also it may be possible with such a guide wire to cross total chronic occlusions in a vessel. Utilizing such a modified guide wire 16 makes it possible for doctors who are very familiar with shaping distal extremities of guide wires to utilize their skills in a similar manner.

In connection with the guide wire 16 of the present invention it should be appreciated that after a physician has been able to perform an angioplasty on a stenosis in a vessel of a patient, it is possible for the physician to partially retract the guide wire 16 and to thereafter advance the distal extremity of the guide wire into another vessel utilizing the same procedure. This makes it unnecessary for the physician to withdraw the guide wire in treating stenoses in multiple vessels during an angioplasty procedure. This again reduces the time required for physician and the amount of time which the patient is subjected to fluoroscopy.

In connection with the present invention it should be appreciated that in addition to utilizing Nitinol for the actuator wire 64 in the guide wire 16 and with the core wire 28 being formed of stainless steel, the core wire can also be made out of a superelastic Nitinol or other alloys which can provide additional stiffness to the tip. A platinum foil can also be used which can be provided with a predetermined curvature which will straighten out when a current is passed through the same. The use of superelastic materials in the present application is particularly desirable because the superelastic material has a memory to return to the same shape every time the shape memory material is heated. It is very predictable in achieving the same desired angle upon heating. Thus, even if the superelastic material is shaped with a predetermined memory as for example an angle 45° or 90°, it will return to such an angle when heat is applied to the same.

Polyimide coatings have been selected in connection with the present invention because they have a very high elastic strain compared to other conventional polymers. This is particularly desirable because of space limitations. It is desirable to reduce the thickness of the insulating coating to the smallest possible dimension while achieving the desired insulation. In addition, polyimides have very good antifriction properties. The polyimide is also a very tough material. Since it is a cross-linked polymer, it has improved adhesion characteristics to the stainless steel core wire.

In FIG. 12 there is shown a guide wire 151 incorporating another embodiment of the present invention. It differs from the guide wire 16 hereinbefore described principally in that the inner sleeve 42 and the coil-spring 61 have been replaced by a counterwound coil assembly 152. Counterwound coil assemblies are disclosed in co-pending application Ser. No. 08/629,060 filed on Apr. 8, 1996.

The counterwound coil assembly 152 consists of first and second counterwound coils 153 and 154 with the coil 153 being the exterior coil and coil 154 being the interior coil. The counterwound coil assembly 152 can have the suitable length as for example 30 centimeters and is secured to the distal extremity 24 of the flexible elongate tubular member 22. The two coils 153 and 154 are formed of a suitable material such as stainless steel identified as SS 304V which is characterized in that it has a very high tensile strength, it is very springy and has a very high modulus of elasticity. For the coils, a drawn ribbon is used. The ribbon has a thickness of approximately 0.00075" and a width of 0.006" to provide at least a ratio of 1 by 8 for thickness with respect to width to obtain a stiffer coil having the desired column stiffness. As can be seen from FIG. 12 of the drawings, the coils 153 and 154 are wound in opposite directions with the coil 153 being wound in a clockwise direction and the coil 154 being wound in an opposite or counter-clockwise direction. Typically, this is accomplished by winding the outer coil 153 on a mandrel rotating in one direction as for example clockwise, releasing the ends of the wound coil 15 and putting it aside. Thereafter utilizing the same mandrel the other coil 154 is wound in the opposite or counter-clockwise direction. While the inner coil 154 is still wound on the mandrel, it can be inserted through the outer coil 153 and then released so that the outer surface of the coil 154 engages the inner surface of the coil 153 to establish frictional engagement between the two coils 153 and 154.

The counterwound coil assembly 152 can then be mounted on the distal extremity of the inner mandrel or core wire 28 and secured thereto by suitable means such as an adhesive or a solder (not shown). The other components of the guide wire 16 as hereinbefore described extend through the bore 156 in the coil assembly 152 and the distal extremity of the flat 57 and the distal extremity 68 of the actuator wire 64 are bonded into a ball-like tip 158 in a suitable manner such as by a plasma weld. A layer 161 of a suitable material such as a polyimide can be placed over the coil assembly 152 to prevent the entry of blood or other liquids in the vessel and to which the guide wire 151 is to be inserted.

The guide wire 151 utilizing the counterwound coil assembly 152 has excellent torque transmission which is provided by the counterwound coils 153 and 154 making it possible to transfer torque in a clockwise or counter-clockwise direction as the guide wire 151 is rotated. The guide wire 151 can be utilized in the same manner as the guide wire 16 hereinbefore described. The guide wire 151 provides improved torque capabilities principally because of the counterwound coil assembly 152 on the distal extremity of the guide wire 151.

If there is sufficient room available, it should be appreciated that additional coils can be provided within the counterwound coil assembly 152. For example a third coil could be provided (not shown) within the inner coil 154 going in the same direction as the coil 153. Similarly, a fourth coil can be provided within the additional coil and wound in the same direction as the coil 154. The use of additional counterwound coils is particularly appropriate in the larger size guide wires from 0.018" and larger.

Figure 13:
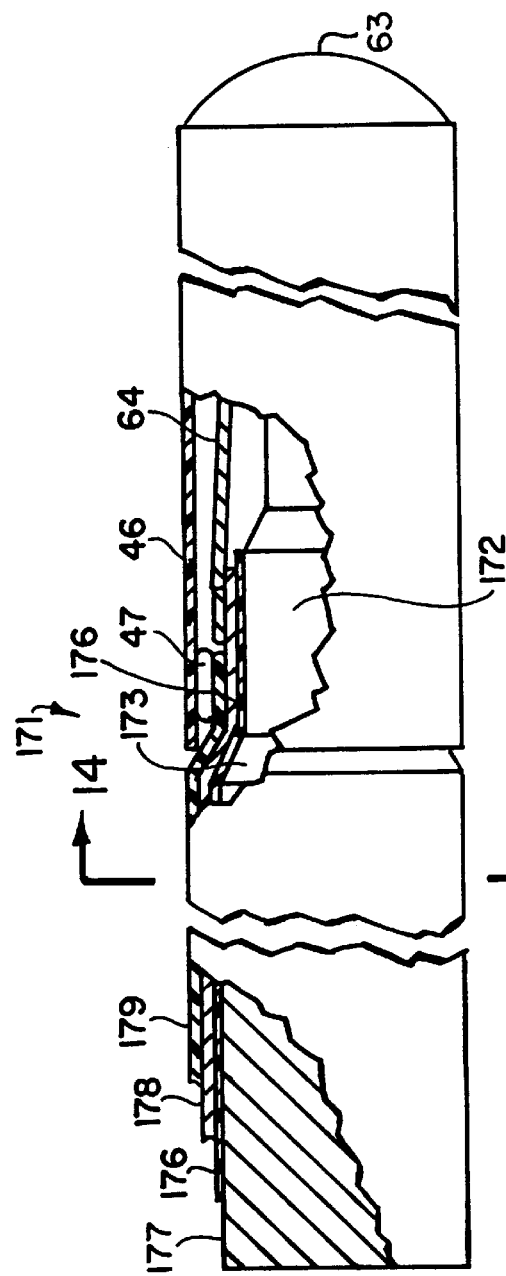
FIG. 13 is a partial side-elevational view showing the distal extremity of another embodiment of a guide wire incorporating the present invention.
Figure 14:
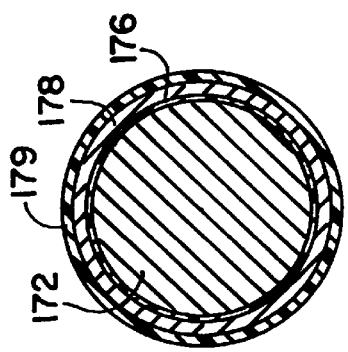
FIG. 14 is a cross-sectional view taken along the line 14—14 of FIG. 13.

Another embodiment of a guide wire incorporating the present invention is shown in FIGS. 13 and 14. The guide wire 171 is very similar to the guide wires hereinbefore described, the principal exception being that the flexible elongate tubular member 22 in the form of a hypotube has been omitted to permit use of a larger diameter core wire that is provided to aid in torque transmission. Thus, as shown in FIGS. 13 and 14 a core wire 172 has been provided of a suitable material such as stainless steel which has a suitable outside or predetermined diameter such as 0.013" extending to the first taper 173 having a suitable length as for example 145 centimeters. As shown in FIG. 14, the core wire 172 is solid. The distal extremity of the core wire 172 is of a reduced size or diameter in comparison to the outside or predetermined diameter and is provided with various tapers of the type described in connection with the embodiment of the guide wire shown in FIG. 1 and is connected to the plasma weld 63 in the manner hereinbefore described. An insulating layer 176 is provided on the outer surface of the core wire 172 and extends from the proximal extremity to leave a cylindrical portion 177 uncovered, as for example a length of 1 cm and extends towards the distal extremity and underlies a metal layer 178 provided on the core wire 172. The insulating layer 176 is formed of a suitable material such as a polyimide of a suitable thickness as for example 0.0003". This uncovered cylindrical portion 177 is provided for making electrical contact to the guide wire 171 to supply electrical energy to the actuator wire 64 in the manner hereinbefore described.

A conductive metal layer 178 is placed over the insulating layer 176 and extends from regions near opposite ends of the insulating layer 176. The conductive metal layer 178 can be formed of a suitable conductive material as for example 0.0005" of silver or copper. A more suitable conductive layer can be comprised of 1 to 2 microns of nickel to serve as an adhesion layer followed by 5 to 6 microns of copper and covered by a thin layer of gold as for example layer having a thickness of less than 1 mil. The conductive metal layer 178 is covered with a layer 179 of a suitable insulating material such as parylene, polyethylene or PET which leaves the cylindrical distal extremity of the conductive metal layer 178 exposed (see FIG. 13) and which has the other extremity underlying the outer sleeve 46 and bonded thereto by the adhesive 47 as described in the previous embodiments. The actuator wire or member 64 extends along the core wire 172. The proximal extremity of the actuator wire or member 64 is bonded to the conductive metal layer 178 and is thereby secured to the core wire 172 as shown in FIG. 13. The distal extremity of the actuator wire or member 64 is secured to the tip 63 and thereby to the distal extremity of the core wire 172.

Thus it can be seen in the embodiment of the guide wire 171 as shown in FIGS. 13 and 14, that electrical energy can be supplied to the actuator wire 64 by utilizing the stainless steel core wire 172 for one of the conductors by making contact with region 177 through the core wire 172 through the plasma weld 63 and then through the actuator wire 64 which is bonded to the conductive metal layer 178 to provide the other electrical connection at the distal extremity which can make a connection to a suitable connector (not shown) so that electrical energy from the control console 18 can be supplied to the guide wire for operation in the same manner as hereinbefore described in connection with the previous embodiments.

From the foregoing can be seen that providing a conductively cladded core wire makes it possible to utilize a larger core wire or mandrel to enhance the torque characteristics of the guide wire. This is particularly advantageous for small size guide wires as for example 0.014" of the type shown in FIGS. 13 and 14 as well as for smaller diameter guide wires. The construction shown in FIGS. 13 and 14 is also advantageous in that it is more economical to construct.

A guide wire 201 incorporating another embodiment of the invention is shown in FIGS. 15, 16 and 17. As shown therein, the guide wire 201 consists of a flexible elongate member 202 in the form of a core wire or mandrel formed of a suitable material such as stainless steel and having a diameter ranging from 0.0005" to 0.010" and preferably approximately 0.0075" and having a proximal extremity (not shown) and a distal extremity 204. The distal extremity 204 is provided with tapered and flattened portions as hereinbefore described in connection with the embodiment shown in FIG. 2. The core wire or mandrel 202 can have a suitable length as for example 180 cm.

As hereinafter described, the core wire or mandrel 202 can serve as a conductor. Additional conductive means is carried by the core wire or mandrel for providing a second conductor and consists of an insulation layer 206 formed of a suitable material such as a polyimide which is coated onto the outer surface of the core wire or mandrel 202. The conductive metal layer 207 is formed-on the insulation layer 206 and is formed of a suitable conductive material such as silver. The silver layer 207 can be applied in a suitable manner such as by soldering or alternatively by a less expensive process called mirroring or a silver ink dip process. In this process, the insulation layer 206 is treated to form a proper bond with the silver to be formed thereon. This bond is formed by a coat of sugar, typically sucrose, glucose, formaldehyde, etc. This coating can be accomplished by dipping the flexible elongate member in the form of a core wire or mandrel into a room temperature bath. If for example the bath is a long chain sugar such as formaldehyde, the bath in liquid form will coat the polyimide insulating layer with a liquid layer which is then partially cured in a suitable manner such as by the use of ultraviolet light so that aldehyde groups are hanging off of the surface.

After the coating has been partially cured, the core wire or mandrel 202 can be dipped into a silver nitrate solution. Silver from the silver nitrate solution is deposited onto the coating. The formaldehyde serves to form a strong mechanical bond between the polyimide insulating layer and the silver layer to create good adhesion between the same. During the dipping process, the silver nitrate can be agitated and maintained at a desired temperature as for example 30° C. to 40° C. to cause the deposition of silver to occur at a faster rate than at lower temperatures. When the silver is deposited in this manner, it will adhere more tightly to the polyimide insulation layer 206 than to the core wire or mandrel 202. The insulation layer 206 can have a suitable thickness as for example 0.5 to 2 mils and similarly the conductive metal layer 207 formed of silver can have a suitable thickness as for example 0.5 to 2 mils. A flexible elongate tubular member 211 of the type hereinbefore described and in the form of a stainless steel hypotube is coaxially mounted on the core wire or mandrel 202. An adhesive 212 is disposed on the proximal and distal extremities of the hypotube 211 to bond the hypotube to the core wire 202 to aid transmission of torsional forces between the proximal extremity of the guide wire 201 and the distal extremity.

The distal extremity of the hypotube 211 is provided with a taper 213 extending forwardly and inwardly as shown in FIG. 15. An insulation layer 216 is provided on the outer surface of the hypotube 211 and is formed of a suitable material such as a polyimide. The hypotube 211 has a suitable wall thickness, as for example 2 mils, so that for a hypotube to have an inside diameter of 0.010", the outside diameter would be 0.014".

A flexible coil assembly 221 is mounted on the distal extremity of the mandrel or core wire 202 and is secured to the distal extremity of the hypotube 211. The flexible coil assembly 221 can have a suitable length as for example 35 cm with the guide wire 201 having a total length of 180 cm. The coil assembly 221 is provided in two sections, a proximal section 222 and a distal section 223 in which the distal section can have a suitable length as for example 5 cm.

The proximal section 222 of the coil assembly 221 can be formed of a less expensive material such as copper whereas the distal extremity 223 is formed of a suitable radiopaque material such as platinum or platinum tungsten alloy. The coils 222 and 223 can be formed of a wire of a suitable diameter as for example 0.0225" or 2.5 mils. Before winding the coils, portions of the wire can be flattened to provide flattened coil sections 222a and 223a respectively, with the flattened portions being provided on the proximal extremities of the respective sections 222 and 223. As shown in FIG. 15, the flattened portions 222a are inserted into an annular space 224 provided between the interior of the hypotube 211 and the exterior of the core wire 202 and are electrically connected to the hypotube 211 by suitable means such as solder 226. The section 222 extends coaxially over the core wire 202 and the distal section 222 abuts the proximal extremity of the section 223 which is also coaxially disposed on the core wire 202. The distal extremity of section 223 is secured in a suitable manner such as by a plasma weld 228 formed of a conductive material which is bonded to the distal extremity of the core wire 202 which has the insulation layer 206 removed therefrom so that it makes electrical contact with the plasma weld 228. The plasma weld 228 provides a hemispherical or rounded outer surface 229.

Plasma weld 228 also makes electrical contact with an actuator member 231. The actuator member 231 in connection with the present embodiment is of a reduced length as for example 5 to 7 cm in comparison to approximately 20 cm for the embodiments hereinbefore described by improving radial symmetry. This aids in reducing any tendency for the guide wire to whip during use as hereinafter described. The actuator member 231 is formed of a wire 232 of a suitable Nitinol material which is covered with a layer of insulation 233 formed of a suitable material such as a polyimide. The wire 232 can have a suitable diameter, as for example 2.5 mils. The distal and proximal extremities of the actuator member 231 are not insulated and are respectively electrically coupled to the weld 228 and to the distal extremity of the coil section 222 by solder 236. It can be seen that by providing the flattened portion 223a for the distal spring section 223 it is possible to provide the necessary space for the actuator member 231.

The distal extremity of the distal coil section 223 is filled with a suitable silicone encapsulant 238 disposed between the weld 228 and an adhesive connection 239 which is provided for securing the coil section 223 to the core wire 202.

Operation and use of the guide wire 201 as shown in FIGS. 15, 16 and 17 is very similar to that hereinbefore described. However the embodiment of the guide wire 201 has certain additional advantages. As in the previous embodiment, it has a unique body design in which the core wire 202 is bonded to the hypotube 211 so as to act as a unitary structure in the transformation of torsional forces from the proximal extremity of the guide wire 201 to the distal extremity and to the flexible coil assembly 221. The tendency of the guide wire to whip is greatly minimized by the use of the conductive means for the actuator member 231 coaxially disposed in the guide wire. One of the conductors is coaxially carried by the core wire 202 and the other conductor is provided by the hypotube 211 which is also coaxially disposed in the guide wire. This overcomes any eccentricity which is provided when two separate conductors as for example conductor wires are disposed within the guide wire. The only remaining eccentricity of the guide wire as shown in FIGS. 15, 16, and 17 is that provided by the actuator member 231 which as hereinbefore described has been shortened substantially so that its offsetting effect during torsional movement of the guide wire is greatly minimized.

In the event it is desired to provide additional conductors in the guide wire, another embodiment of a guide wire 241 is shown in FIG. 18. In such an embodiment, the exterior surface of the core wire 242 could be coated with a silver layer 243 in the manner hereinbefore described followed by an insulating layer 244 followed by another silver layer 246. The silver layer 246 is covered by an insulation layer 247. All of these layers are disposed within a hypotube 248 covered by an insulation layer 249. In this manner it can be seen that a plurality of coaxial conductors can be provided on the core wire in a manner hereinbefore described and still provide the desired radial symmetry. This minimizes any tendency of the guide wire to whip during torsional rotation. These additional conductors can be utilized for additional features in the guide wire for example for providing steering capabilities in the distal extremity by the use of shape memory elements in the distal extremity in a manner well known to one of ordinary skill in the art. This also serves to inhibit any preferential bending of the guide wire in one direction or another.

In connection with the foregoing invention, in the event that pinholes occur in the various coaxial layers formed on the core wire and through which minuscule connections are made between the conductive layers through such pinholes, the connections can be eliminated by applying electrical energy between two layers at a time so as to fuse or evaporate any short circuits which may be present between the two conducting layers because of such connections. Vaporizing or blasting out these small connections establishes the continuity of each of the conductive layers so that it can be utilized for a conductor in the manner hereinbefore described.

Although the present conductive layers have been described principally with the use of silver, it should be appreciated that other materials can be utilized for the conductive layer. Also, a composite conductive layer can be provided as for example a layer of copper which has been coated with gold with a nickel adhesion layer therebetween which promotes adhesion and which also prevents migration of the copper into the gold.

Another embodiment of a guide wire with adjustable stiffness incorporating the present invention is shown in FIGS. 19–20. As shown therein, the guide wire 261 consists of a flexible elongate member 262 in the form of a core wire 262 formed of stainless steel 304 having proximal and distal extremities 263 and 264. The core wire 262 is solid. The proximal extremity 263 of the core wire 262 is provided with a predetermined outside diameter as for example ranging from 0.010" to 0.032" and preferably a diameter of 0.012". The distal extremity 264 of the core wire 262 is centerless ground to provide portions of reduced diameter with respect to the predetermined outside diameter. Thus, the distal extremity 264 is provided with portions 264a, 264b and 264c of progressively reduced diameters, as for example 0.09", 0.0055" and 0.0025", respectively, and a flattened distal portion 264d having a width of 0.0015" and a thickness of 0.0001". As shown, the portions 264a, 264b, 264c and 264d are cylindrical in shape with tapered transitions extending therebetween. The core wire 262 can be of a suitable length, as for example 135–275 cm. and preferably approximately 175 cm.

An insulating layer 266 formed of a suitable material such as a polyimide is provided on the outer surface of the core wire 262 and extends from the proximal extremity 263 leaving a small annular space 267 on the proximal extremity 263 free of insulation to the distal extremity 264 and just beyond the portion 264b. The insulating layer 266 can have a suitable thickness ranging from 0.003" to 0.002" and preferably approximately 0.0005". A conductive layer 268 overlies the insulating layer 266 and extends just slightly beyond the portion 264a. This conductive layer 268 can be formed of suitable material such as a silver conductive ink of the same thickness as the polyimide layer 266.

A cylindrical tube-shaped actuator member 271 is formed of a suitable material such as a temperature variable superelastic Nitinol or other superelastic ordered intermetallic alloy having a Young's modulus ranging from $4 \times 10^6$ to $14 \times 10^6$ psi. The material has a Young's modulus in a soft martensitic state of $4$–$6 \times 10^6$ psi and a stiff or austenitic state ranging from $10$–$14 \times 10^6$ psi. The actuator member 271 can have a suitable outside diameter of, for example 0.010" to 0.013" and preferably 0.0125" and 0.009" to 0.010" inside diameter to provide a wall thickness of 0.001" to 0.002" and preferably 0.00175". This actuator member 271 can have a suitable length, as for example from 3–10 cm.

In one embodiment of the present invention, the sleeve has a wall thickness of 0.0025" thinned down to a thickness ranging from 0.001" to 0.0015" by centerless grinding after which the sleeve is cut down to the desired length and the edges rounded. Thereafter a mandrel of a suitable material such as stainless steel having the desired size is inserted into the sleeve 36. The mandrel is used to keep the tube or sleeve 36 straight and circular rather than oval-shaped or elliptical so that it will not deform during heat treatment as hereinafter described. Thus the mandrel can have an outside diameter of for example 0.0085" to 0.009". The sleeve 36 with the mandrel therein is placed in a conventional oven and heat treated for a period of time ranging from 30 to 60 minutes and preferably 20 to 30 minutes at a temperature ranging from 300° to 600° C. and preferably 440° C. After this heat treating operation has been completed, the superelastic sleeve 36 is removed from the oven and quickly cooled, after which the mandrel is removed. The sleeve is relatively rigid prior to the heat treating operation, whereas after the heat treating operation hereinbefore described, the sleeve is very flexible and pliable. As is well known to those skilled in the art of superelastic materials, the elastic material before the heat treatment is in the austenitic phase at room temperature whereas after heat treatment it is transformed into the martensitic phase at room temperature. Thus, by the heat treatment step hereinbefore described, the superelastic material is transformed from the austenitic phase to the martensitic phase so it is quite floppy and flexible at room temperature and will only assume the austenitic phase and become stiff when subjected to heat as hereinafter described.

The proximal extremity 272 of the actuator member 271 after it is heat treated is slid over the silver conductive layer so that it is in electrical contact therewith and also is coupled to the core wire 262 through the conductive layer 268 and insulating layer 266. As shown, the distal extremity 273 of the actuator member 271 extends distally just beyond the termination of the insulating layer 266. A small conductive metal coil 276 formed of a suitable material such as silver is placed within the distal extremity 273 of the actuator member 271. A tube 278 formed of a suitable insulating material such as a polyimide and having a suitable size as for example an inside diameter of 0.0130" and an outside diameter of 0.140" and a suitable length as for example 20.5 cm is slid over the actuator member 271 and over the conductive layer 268 to the proximal extremity of the portion 264a of the distal extremity 264 of the core wire 262.

A platinum radiopaque tip coil 281 having a proximal extremity 282 and a distal extremity 283 is provided. The proximal extremity 282 abuts the distal extremity 272 of the actuator member 271 and is secured thereto by suitable means such as a silver solder which bonds the coil 281 to the actuator member 271 and to the interior coil 276. A hemispherical tip 286 is formed by solder 286 which bonds the distal extremity 283 of the coil 281 to the portion 264d of the core wire 262.

With the construction shown, it can be seen that there is provided an air gap 287 between the solder 284 at the distal extremity 273 of the actuator member 271 and the silver conductive layer 268. Thus, it can be seen that the distal extremity 273 of the actuator member 271 is electrically connected to the core wire 262 whereas the proximal extremity 272 of the actuator member 271 is electrically in contact with the conductive layer 268 so that the electrical means hereinbefore described can provide electrical energy to the conductive layer 268 and to the bare coil wire portion 267. The polyimide tube 278 serves to provide a smooth transition from the tip coil 281 back to the tapered core wire 262. It also serves to electrically isolate the electrical circuit which is formed to supply electrical energy to the actuator member 271. It also acts as a thermal barrier from the heat generated in the actuator member when it is actuated electrically.

Operation and use of the guide wires shown in FIGS. 19 and 20 may now briefly be described as follows. The tip of the guide wire will be bent in a conventional manner in the shape desired by the physician. The guide wire can be advanced through an introducer into the vasculature of the patient, as for example into an arterial vessel in which a stenosis or lesion is present. Generally, the distal extremity of the guide wire can be very floppy, which floppiness is not substantially inhibited by the use of the tubular actuator member 271. This is true because the tubular actuator member 271 has a relatively thin wall thickness permitting it to flex. If it is desired to increase the stiffness of the distal extremity of the guide wire, it is merely necessary to supply electrical energy to the actuator member 271 from the controller 289. This can be accomplished by supplying a desired current level to the actuator member for a period of time to retain the stiffness of the actuator member 271. Since the mass of the actuator member 271 is relatively small, this stiffness is created substantially instantaneously in real time, for example within 1–2 seconds. The current supply can also be adjusted, for example from 200–280 milliamperes. As soon as current flow is terminated, the actuator member 271 cools permitting the guide wire to return to its natural floppy state in its distal extremity. Thus, it can be seen that there has been provided a guide wire in which the stiffness of the distal extremity can be greatly increased when desired.

In connection with the present invention, it has been found that several Nitinol alloys can be utilized. One which is found to be satisfactory is an Alloy K or shape memory alloy supplied by Raychem Corporation of Menlo Park, Calif. It is a ternary alloy, it is a copper-containing nickel-titanium alloy. However, it has been found that its stiffness characteristics are less desirable than a binary superelastic alloy, which is identified as Alloy BB from Raychem Corporation of Menlo Park, Calif. By utilizing this Alloy BB, it has been found that optimum stiffness characteristics can be obtained when the guide wire is activated and the desired floppiness is obtained when the guide wire is not activated. In other words, before activation the guide wire acts in a manner similar to a conventional floppy guide wire, whereas when activated it acts as one of the stiffer guide wires presently in the marketplace.

In FIG. 21 there is a graph showing the adjustable stiffness which can be achieved utilizing the BB alloy. This adjustable stiffness has been calibrated in bend force in grams versus a distance from the tip of the guide wire. Thus as shown, since the actuator member 271 is spaced a predetermined distance from the tip, as for example the 3 cm shown, the change in stiffness is set forth in conjunction with the length of the actuator member 271 from the 3 cm. Thus it can be seen in this region the activation of the 20.5 cm actuator member 271 of the guide wire has a floppiness as indicated by the non-activated line 291. A substantial increase in stiffness is shown when the actuator member 271 is activated as represented by the line 292 in FIG. 21. As soon as the actuator member 271 is deactivated, the guide wire returns to its non-activated floppy state. Conversely, as soon as it is again activated, it returns to the activated state shown by line 292.

From FIG. 21 it can be seen that the bend force in grams changes as a function of distance from the tip of the guide wire. Thus, for the first few centimeters, up to 3 cm. from the tip the guide wire is very floppy and there is no change when the actuator member 271 is actuated. As explained previously, this is because the Nitinol actuator member 271 does not extend to within 3 cm of the tip of the guide wire. In the non-activated state, the stiffness is relatively constant until another taper in the grind of the core wire is reached, after which because of the increased cross-sectional area of the core wire, the stiffness increases. When the actuator member 271 is activated, the stiffness of the guide wire along the length of the actuator member 271 increases dramatically, largely overcoming the effects of gradations in the grinding of the core wire.

It has been found that providing an actuator member in the form of a tubular member or hypotube is very advantageous. In addition to dramatically increasing the stiffness of the portion of the guide wire in which it is present, the tubular member or tube is also easy to manufacture and can be readily incorporated into the guide wire. It can be readily put in place with electrical connections being made to opposite ends of the same for activation with electrical energy. Even though the actuator member 271 in the form of a hypotube, it does in fact not stiffen the core wire in the vicinity of the actuator member because any small increase in stiffness can be readily compensated for by increasing the grind to provide a larger diameter-air space between the core wire and the interior of the actuator member 271. Thus it can be seen that any increase in stiffness imparted by the tubular actuator member 271 can be compensated for by additional grinding of the core wire so that the overall stiffness of the guide wire remains the same in an inactivated condition. When activated as explained previously, the stiffness of the guide wire changes dramatically in the region in which the actuator member 271 is positioned.

If desired, as shown in the drawings a lubricous coating (not shown) of a suitable such as Teflon can be applied to the exterior surface of the guide wire 261 to enhance the capability of the guide wire 261 to transverse vessels in the patient. The coating can have a thickness ranging from 0.0005" to 0.001".

Operation and use of the adjustable deflection guide wire 261 with adjustable support characteristic or adjustable stiffness proximal of the tip coil 276 may now be briefly described as follows. At room temperature, the distal extremity of the guide wire 261 is very floppy and has characteristics comparable to floppy guide wires presently in the marketplace. Let it be assumed that it is desired to perform a conventional angioplasty procedure in which an entry is made into the femoral artery of the patient and a guiding catheter is inserted therein. Thereafter, the guide wire 261 of the present invention is introduced into the coronary vessel of the patient through the guiding catheter in a conventional manner utilizing the floppy characteristics of the guide wire to pass through tortuosities if present in the vessel until the distal extremity is disposed in the stenosis or occlusion in the vessel. A conventional balloon catheter (not shown) can then be advanced over the guide wire 11 after it has been positioned in the desired location with the balloon catheter tracking the guide wire until the balloon has been advanced into the stenosis to be treated in the angioplasty procedure. The balloon of the balloon dilatation catheter can then be inflated one or more times to enlarge the opening through the stenosis.

Thereafter, let it be assumed that it is desired to place a stent in the stenosis to aid it in remaining open and so that restenosis will not occur, the balloon dilatation catheter can be removed leaving the guide wire 261 in place. A stent delivery catheter is then advanced over the guide wire 261.

In order to provide additional support for the stent delivery catheter, electrical energy is supplied to the Nitinol sleeve 271 from a power supply 56 to supply electric current directly to the Nitinol sleeve 271 to heat the same to a temperature above 55° C. but below 100° C. so that the superelastic alloy material in the sleeve 271 is transformed to the austenitic state to progressively stiffen the same as the temperature increases and to thereby progressively stiffen the distal extremity of the guide wire 261. This stiffening serves to prevent the distal extremity of the guide wire 261 from collapsing or prolapsing. The stent (not shown) is delivered into the stenosis by the stent delivery catheter. After the stent has been advanced over the stiffened guide wire 261, the stent can be positioned in a conventional manner and left in place and the stent delivery catheter removed after which the guide wire 261 also can be removed to complete the medical procedure.

By using the guide wire of the present invention, it is only necessary to utilize one guide wire because the guide wire has a distal extremity with an adjustable support characteristic or adjustable stiffness in that it can be very floppy at room temperature or at the temperature of the human body when in blood in a vessel. It can be stiffened to provide additional support during the time it is desired to deliver a stent by supplying electrical energy to the Nitinol sleeve or actuator member 271 to heat the same. It should be appreciated that if desired, rather than supplying electrical energy directly to the stent, electrical energy can be supplied to a heating element (not shown) either on the inside or on the outside of the sleeve to heat the same to also cause it to assume an austenitic or stiff characteristic.

From the foregoing, it can be seen that there has been provided a guide wire with adjustable stiffness in which the stiffness is provided in a portion of the shaft of the guide wire proximal of the coil tip. It is also feasible to provide variable or adjustable stiffness in the tip in the same guide wire as well as in adjustable stiffness proximal of the tip. Such a guide wire 301 is shown in FIGS. 22–23 and consists of a core wire 302 having proximal and distal extremities 303 and 304, respectively, and being sized and ground in the same manner as the core wire 262. It can have a suitable length, as for example ranging from 140–300 cm. An insulating layer 306 formed of a polyimide is provided on the exterior surface of the core wire 302. The polyimide insulating layer 306 can have a suitable thickness as for example 0.005". A conductive ink layer 307 is provided on the insulating layer 306. If desired, an insulation layer (not shown) can be provided over the conductive ink layer 317.

A first actuator member 311 in the form of a tube formed of Nitinol as hereinbefore described is slid over the top of the distal extremity of the conductive layer 307 as shown in FIG. 22 to make electrical contact therewith. A polyimide insulating tube 314 having a suitable outside diameter as for example 0.012" is slid over the top of the actuator member 311 and is advanced proximally until it extends over the tapered portion 306*a* of the insulating layer 306 as shown in FIG. 22.

A second actuator member 316 is provided which is formed of Nitinol ribbon having a suitable cross-section as for example a width of 0.004" (4 mils) and a thickness of 0.002" (2 mils). The second actuator member 316 is provided with proximal and distal extremities 317 and 318. An insulating sleeve 319 is provided on the second actuator member 316 and extends over a suitable distance as for example 2.7 cm but leaving portions of the proximal and distal extremities bare so that electrical contact can be made with the second actuator member 316 while still insulating the second actuator member 316 from a coil 321 having proximal and distal extremities 322 and 323 and through which the second actuator member extends. The coil 317 is formed of a suitable radiopaque material such as platinum or a platinum alloy and has a suitable length, as for example 3 cm. The proximal extremity 322 of the coil 321 abuts the distal extremity of the first actuator member 311 in the form of a Nitinol hypotube which is bonded thereto by a conductive solder 326 which also bonds the proximal extremity 317 of the second actuator member 316 to the interior distal extremity of the first actuator member 311 so that it is physically and electrically connected thereto.

In the guide wire shown in FIGS. 22–23, a binary alloy, as for example Alloy BB is utilized for the first actuator member 311 whereas a ternary alloy, as for example Alloy K, is utilized for the second actuator member 316.

A joining ring 327 formed of a suitable material such as silver is provided and is sized so that it can fit within the distal extremity 323 of the coil 321. A plasma weld 328 then is used to join the joining ring 327 to the distal extremity 323 of the coil 321 and also to form an electrical and physical connection between the distal extremity 304 of the core wire 302 and the distal extremity 318 of the actuator member 316 so that the core wire 302 is electrically connected to one end of the second actuator member 316 which has its other end connected to the first actuator member 311 that is electrically connected to the conductive layer 307. This permits electrical energy to be supplied to the first and second actuator members 311 and 316 by making appropriate connections as hereinbefore described to the bare portion of the proximal extremity of the core wire 302 and the exposed conductive layer 307. A thin layer of a suitable ultra-gviolet cured adhesive 329 is placed over the plasma weld to form a smooth, rounded generally hemispherical surface.

Thus in the guide wire 301 there has been provided a variable stiffness deflectable tip and adjustable deflection guide wire in which an adjustable stiffness or an adjustable support characteristic can be provided in the shaft portion of the guide wire proximal of the coil 321 to in effect provide an adjustable support. The first and second actuator members 311 and 316 are connected in series so that the current passes through the core wire 302 to the tip of the guide wire 301, through the plasma weld 328, through the Nitinol ribbon forming the second actuator member 316, through the Nitinol hypotube 311, through the conductive layer 307 to the proximal extremity of the guide wire 301 into the electrical connector utilized in connection with the guide wire as hereinbefore described. With this series connection, it is still possible to adjust the stiffness of the shaft and also bend the guide wire at the tip. This is made possible because the Nitinol ribbon forming the second actuator member 316 has a smaller mass than the hypotube forming the first actuator member 311. Thus it is possible to pass sufficient current through the second actuator member 316 to cause deflection of the tip without significantly affecting the stiffness provided by the second actuator member 316. Thus, by appropriately controlling the current flow it is possible to bend the tip by activating the first actuator member 311 and maneuvering the guide wire tip through the tortuous vessel in the body. When it becomes necessary to stiffen the shaft in the vicinity of the coil 321, additional current flow can be applied to cause stiffening of the first actuator member 311 to provide the additional stiffness desired. By way of example, it has been found that 160–200 milliamperes can be utilized for adjusting the bend by activation of the second actuator member 316. The first actuator member 311 can be stiffened by passing additional current, as for example from 200–280 milliamperes and more typically from 220–280 milliamperes.

It should be appreciated that if desired the second actuator member 316 can be formed of Nitinol having a shape memory corresponding to a predetermined bend which may be desired in the distal extremity of the guide wire tip with the amount of the bend being adjustable by the amount of current flowing through the second actuator member 316. Thus it can be caused to bend in a direction which is perpendicular to the flat side of the ribbon utilized for the second actuator member 316. It also has adjustable stiffness. When it is deactivated, it will lose its stiffness and will be returned to a normally straight position by the force provided by the core wire 302. On the other hand, the first actuator member 311 when deactivated is relatively flexible but normally has a straight configuration which is also the configuration it assumes when it is stiffened as electrical energy is applied to heat the Nitinol alloy.

From the foregoing it can be seen that two separate conductors can be provided that the first actuator member 311 and the second actuator member 316 can be independently controlled. In the guide wire 331 shown in FIGS. 24 and 25, the conductive layer 307 can be formed to provide two conductors. After the ink conductive layer 307 has been placed, portions of the ink layer 307 are removed or ground away to provide diametrically opposed longitudinally extending slots 332 extending the length of the core wire 302 and through the entire length of the conducting layer 307 to provide two conductive portions 307a and 307b which are insulated from each other. A polyimide insulating layer 333 covers the conductive portions 307a and 307b. One of the actuator members, the first actuator member 311, is in physical and electrical contact with conductor 307a of one of the conductors 307a and 307b. The other or second actuator member 316 is in physical and electrical contact with the other conductor 307b of the conductors 307a and 307b. Thus, the first actuator member 311 and second actuator member 316 are electrically isolated from each other. A flexible, ultra-violet cured RTV adhesive 331 is placed over the coil 321 to permit bending of the coil 321, but closes off the spaces between the coil and serves to prevent blood from entering into the interior of the col during use of the guide wire 341. This prevents cooling of the first and second actuator members during their actuation.

Figure 26:
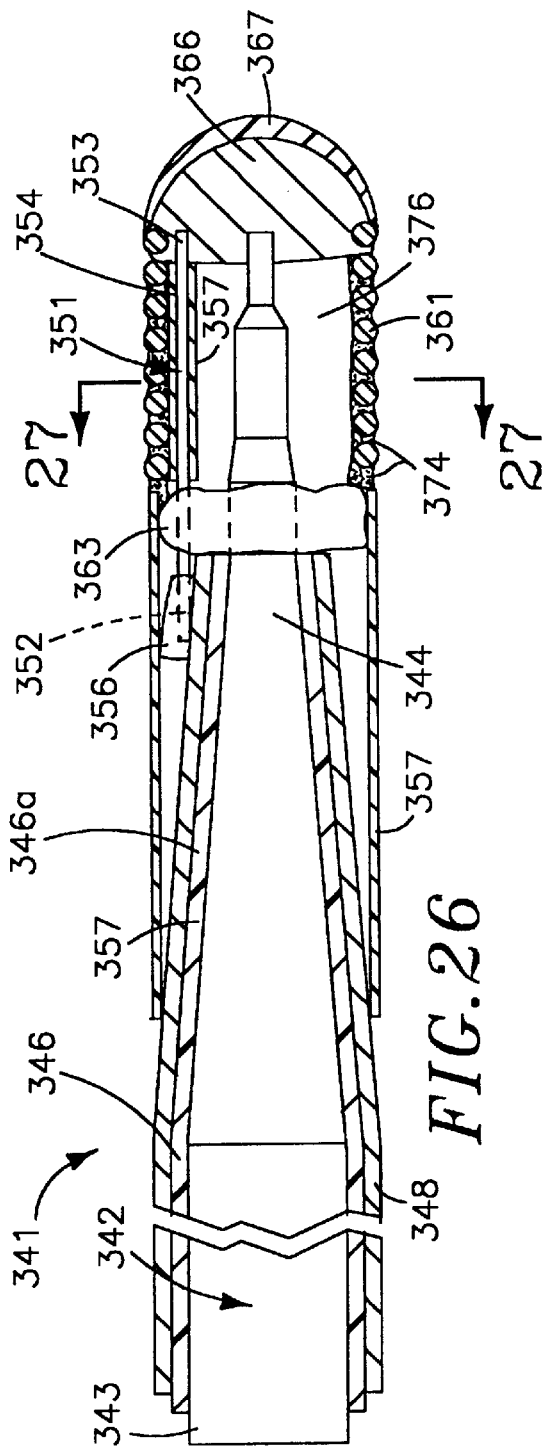
FIG. 26 is a sectional view of still another embodiment of a guide wire incorporating the present invention in which a deflectable tip is provided.
Figure 27:
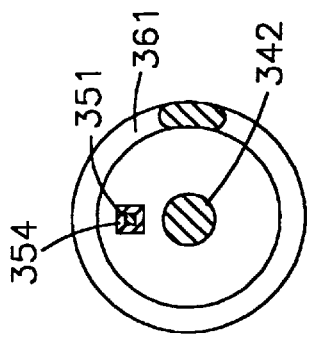
FIG. 27 is a cross-sectional view taken along the line 27—27 of FIG. 23.

Another embodiment of a guide wire incorporating the present invention is shown in FIGS. 26–27. This guide wire 341 consists of a core wire 342 of the type hereinbefore described having proximal and distal extremities 343 and 344 as in previous embodiments of the guide wire of the present invention, a polyimide insulating layer 346 is provided which has a tapered portion 346a at its distal extremity which overlies the outer surface of the core wire 342 as shown. A silver conductive layer 348 is provided on the insulating layer 346.

A Nitinol actuator member 351 is provided which is in the form of a ribbon having a rectangular cross-section, as for example a width of 0.004" and a thickness of 0.002". The actuator member 351 is provided with proximal and distal extremities 352 and 353. An insulating cover or coating 354 formed of a suitable material such as a polyimide extends for substantially the entire length of the actuator member 351 but leaving portions of the proximal and distal extremities 352 and 353 bare so that electrical connections can be made therewith. The proximal extremity 352 is physically and electrically bonded to the insulating layer 356 by a silver epoxy joint 356. The silver epoxy forming the joint 356 is cured in a suitable manner as for example for a period of two minutes at 300° F. A polyimide tube 357 extends over the silver epoxy joint 356 and has an outside diameter of 0.012" so as to provide a smooth transition between the tapered portion 346a of the insulating layer 346. A platinum coil 361 has its proximal extremity 362 abutting the polyimide tube 357 and is bonded to the core wire 342 by an epoxy 363. The distal extremity 364 of the coil 361 is secured to the distal extremity of the actuator member 351 and to the distal extremity 344 of the core wire 342 by a plasma weld 366. An ultraviolet-cured adhesive 367 of a suitable type is placed over the plasma weld 366 to provide a rounded tip for the guide wire.

An adhesive material 374 of a suitable type such as an ultravioletly curable silicon RTV type is placed between the turns of the coil 361 and at least enters partially into the space 376 interior of the coil 361 and between the core wire 302. This insulating material 374 serves a dual function. It serves to provide a liquid barrier between the turns of the coil 361 so as to keep blood in the vessel into which the guide wire is introduced from entering into the space 376. By keeping blood out, the insulating material 374 prevents the blood from cooling the actuator member 351 during the time it is activated. The insulating material 374 also serves to conserve heat which is created within the actuator member 351 making it easier for the actuator member 351 to be initially heated and to retain the heat, thereby reducing the overall current flow required and thus making it easier to actuate the tip. The RTV insulating material 374 is desirable because while providing a liquid barrier and heat insulation, it still has great flexibility thereby permitting bending of the distal extremity of the guide wire as hereinbefore described with the previous embodiments.

Operation and use of the guide wire 341 shown in FIGS. 26–27 is substantially similar to the mode of operation for the guide wires hereinbefore described. The guide wire 341, however, only has the capability for adjusting the stiffness of the coil portion of the guide wire. Thus, a ternary alloy as for example Alloy K can be utilized for the actuator member 351.

Figure 28:
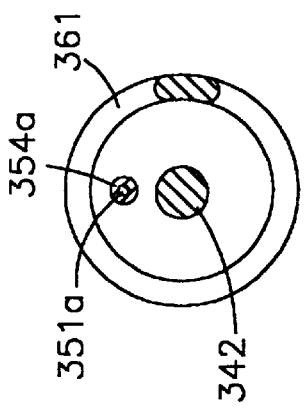
FIG. 28 is a cross-sectional view similar to FIG. 27 showing another embodiment of a guide wire incorporating the present invention.

In FIG. 28, there is shown a cross-sectional view similar to FIG. 25 but showing another embodiment of a guide wire of the present invention which, rather than utilizing an actuator member 51 which is rectangular in cross-section there is provided an actuator member 351a which is circular in cross-section and an insulating layer 354a. Such a guide wire can be shaped like a conventional guide wire by the physician placing an appropriate bend in the distal extremity. After the guide wire has been introduced into the vessel in the body, the tip can be stiffened by supplying electrical energy to the actuator member 351a so as to facilitate passing the guide wire through a totally occluded or a substantially occluded vessel.

Additional embodiments of actuator members which can be utilized in place of the actuator member 351 are shown in FIGS. 29, 30, 31 and 32. Thus, as shown in FIG. 29, there is provided an actuator member 381 in the form of a wedge in which the top and bottom surfaces 382 and 383 are in the form elongate rectangles and the side surfaces 384 and 386 are wedge-shaped or tapered. Thus, there will be gradations in stiffness in directions generally perpendicular to the planar surfaces 382 and 383. The actuator member 381 is also provided with a base 387 which is secured to the ink conducting layer 348 and a tip 388 which is embedded within the plasma weld 366. Thus it can be seen that there is additional flexibility provided substantially perpendicularly to the planes formed by the top and bottom surfaces 382 and 383.

In FIG. 30 there is shown a triangularly shaped actuator member 391 which is provided with top and bottom surfaces 392 and 393 which are triangular in shape and side surfaces 394 and 396 which are rectangular in shape. It is also provided with a rectangular base 397 which would be bonded to the conductive layer 348 and a tip 398 which would be embedded in the plasma weld 366. With such an actuator member 391 it can be seen that the degree of bending and/or stiffness also decreases in a direction towards the tip 398.

Another actuator member 401 is shown in FIG. 31 and is provided with top and bottom surfaces 402 and 403 which are triangular in shape and side surfaces 404 and 406 which are also triangular in shape. It is also provided with a rectangular base 407 which is bonded to the conducting layer 348 and a tip 408 which is bonded into the plasma weld 366. With such an actuator member 401 it can be seen that the actuator member is tapered in two directions along its length to make possible additional gradations in the stiffness provided by the actuator member 401.

An actuator member 411 shown in FIG. 32 consists of top and bottom surfaces 412 and 413 which are triangular in shape and side surfaces 414 and 416 which are also triangular in shape. It is also provided with a square base 417 and a tip 418. Thus it can be seen that the actuator member 411 is in the shape of a pyramid. The base 417 can be bonded to the conducting layer 348 and the tip 418 can be bonded into the plasma weld 366. Thus it can be seen that with the actuator member 411 shown in FIG. 32 there is a gradation provided in two directions at right angles to each other which are substantially the same because of the pyramidal shape.

This gradation in cross-sectional area and mass of the actuator member means that progressing towards the tip of the actuator member there is less material for a higher resistance and therefore a higher rate of heating is achieved, making it possible to deflect the distal extremity of the guide wire with a smaller amount of current. This makes it possible to still deflect the tip of the wire or to stiffen the tip of the wire, but also makes it possible to move the point where the wire starts to bend by moving the point of bending more proximal or more distal depending upon the amount of current which is utilized in activating the actuator member. As the activation current is increased, this current will cause the distal extremity of the guide wire to bend and at the same time will move the radius of bending so that it increases progressively until the bend reaches the proximal extremity of the actuator member. Thus, utilizing the tapered actuator members hereinbefore described, it is possible to change the position of the start of the bend radius. By progressively increasing the current flow through the tapered actuator elements, the commencement of the bend will be moved progressively proximally until the entire actuator member has been incorporated into the bend. Such an adjustable bend location is particularly desirable in traversing particularly tortuous vessels.

It has been found that in connection with the guide wires of the present invention it is possible to ascertain from the proximal extremity of the guide wire whether the guide wire is being activated in air or being activated within a vessel in the human body. This is particularly useful for a physician. The physician wishes to ascertain the characteristics of the distal extremity of the guide wire as it relates to the deflection of the tip or the stiffness of the tip or the stiffness of the distal extremity of the guide wire proximal of the tip coil.

In FIG. 33 there is shown a schematic diagram of electrical circuitry utilized for indicating the environment for the distal extremity of the guide wire. In this connection it has been found that the plasma weld, as for example the plasma weld 336 shown in FIG. 26 serves as a thermocouple 421 shown in FIG. 33. This thermocouple 421 which is provided by the tip plasma weld 366 is connected to the same conductors which supply power to the actuator member 351 which in the embodiment shown in FIG. 26 consists of the core wire 342 and the conductive layer 348 that are connected respectively to lead wires 422 and 423 and connected to an AC power supply 426. The AC power supply 426 provides an AC power output in milliamperes of current at a high frequency sine wave, as for example from 10 kHz to 50 kHz and preferably approximately 33 kHz. The thermocouple 421 generates a DC voltage which can be picked up from the conductors 422 and 423 and supplied through conductors 427 and 428 to a low pass filter 431 to separate the DC voltage from the AC voltage to provide a DC thermocouple voltage output supplied in conductors 432 and 433 to a temperature monitor 436 that provides a reading corresponding to the temperature of the thermocouple 421. From the temperature of the thermocouple 421, the temperature monitor 436 can ascertain whether or not the thermocouple is in air or in the body. If it senses a temperature higher than it normally would be in the body, it is assumed that it is in air and supplies a signal on the conductor 437 to the AC power supply to immediately adjust the AC power supply to an in-air state. This prevents the AC power supply 426 from supplying an unneeded amount of current to the actuator 351 which could possibly damage or destroy the actuator 351. Conversely, if the temperature monitor 436 senses a lower temperature, it then ascertains that the thermocouple 421 must be positioned within the body and causes the AC power supply 426 to be switched to supply additional current to the actuator member 351.

This feature is particularly useful to a physician who is to perform a procedure utilizing a guide wire of the present invention. Assuming that the physician wishes to feel the characteristics of the distal extremity of the guide wire when it is outside the body, the physician can push a switch 438 of the temperature monitor to place the temperature monitor in the air monitoring mode. The physician by then adjusting the output from the AC power supply 426 can ascertain the stiffness and/or deflection desired at the distal extremity. After the physician has properly adjusted the AC power supply 426 to obtain the proper feel at the distal extremity of the guide wire, the physician again operates the switch 438 to return the temperature monitor to its automatic mode at which time it will scale up the current supplied from the AC power supply 426 to provide the same characteristics at the distal extremity of the guide wire as the physician was able to feel when the guide wire was outside of the body.

In view of the foregoing it can be seen that there has been provided a guide wire which has many desirable features. The guide wire has a deflectable tip which can be deflected or bent from a remote location. The deflectable tip can have a shape memory incorporated therein which can be brought into play by the application of heat to the distal extremity. Different bends can be provided in the distal extremity. Also increased stiffness can be achieved. This makes the guide wire of the present invention very advantageous for use in traveling through tortuous vessels and for passing through totally occluded or substantially occluded vessels. Procedures can be accomplished without withdrawing the guide wire from the vessel. Similarly, stenoses in different vessels can be addressed without completely withdrawing the guide wire or reshaping the distal extremity of the guide wire after it has been withdrawn. The guide wire also has very desirable characteristics such as being very floppy with a soft atraumatic tip. Also when desired the distal extremity can be activated to achieve additional stiffness in the distal extremity to facilitate crossing a stenosis.

Also in connection with the guide wires of the present invention it is possible to provide an additional actuator member. Such an additional actuator member is located the guide wire just proximal of the coil to provide additional stiffness and support from the guide wire. This is particularly useful when the guide wire is utilized with a balloon catheter or a stent delivery catheter in which it is desired to impart additional rigidity to the catheter. This can be readily accomplished by activating the additional actuator member to provide the additional stiffness which is translated through the balloon catheter to aid in having the balloon catheter cross a stenosis or to aid in the delivery of a stent carried by the stent delivery catheter, particularly when it is desired to advance the stent into a desired region in the stenosis. Additional capabilities are provided for ascertaining whether the guide wire is in air or in the body to facilitate setting the desired characteristics for the guide wire. The feel which the physician sets in air or outside the body can be achieved within the body.

In connection with the present invention it should be appreciated that although the electrical energy is supplied directly to the actuator members, it is possible to provide a separate heating element adjacent each actuator member for heating the actuator member.

What is claimed is:

1. A guide wire for use in a medical procedure and for use with a power supply comprising a solid core wire having proximal and distal extremities, the proximal extremity having a predetermined diameter, at least a portion of the distal extremity having a reduced size with respect to the predetermined diameter, a flexible coil secured to the distal extremity of the core wire and extending over the portion of the core wire having a reduced size, an actuator member disposed proximal of the coil and extending along the core wire, electrical conductive means extending from the proximal extremity of the core wire and to the actuator member for supplying heat to the actuator member, said actuator member being formed of a temperature activated metal alloy having a Young's modulus of $4 \times 10^6$ to $14 \times 10^6$ psi which increases in stiffness when heat is supplied thereto to increase the stiffness of the guide wire proximally of the coil.

2. A guide wire as in claim 1 wherein said actuator member is in the form of a cylindrical tube encircling the core wire.

3. A guide wire as in claim 1 wherein said electrical conductive means is connected to opposite ends of the cylindrical tube.

4. A guide wire as in claim 1 wherein said temperature activated metal alloy is a binary alloy.

5. A guide wire as in claim 4 wherein said binary alloy is Alloy BB.

6. A guide wire as in claim 1 further including an additional actuator member disposed within the coil and extending longitudinally of the core wire and means carried by the core wire for electrically connecting the additional actuator member to the power supply from the proximal extremity of the guide wire.

7. A guide wire as in claim 6 wherein said additional actuator member is formed of a shape memory nickel titanium alloy.

8. A guide wire as in claim 7 wherein said shape memory nickel titanium alloy is a ternary alloy.

9. A guide wire as in claim 8 wherein said ternary alloy is Alloy K.

10. A guide wire as in claim 6 wherein said first named and additional actuator members are connected in series.

11. A guide wire as in claim 6 wherein said first named and additional actuator members are connected in parallel.

12. A guide wire as in claim 1 wherein said core wire serves as one conductor and wherein the other conductor is provided by a conductive layer formed on the core wire exterior of the core wire.

13. A guide wire as in claim 1 wherein said power supply is an AC power supply and wherein said means connecting the distal extremity of the core wire to the distal extremity of the coil provides a thermocouple generating a DC current when electrical energy is supplied to the actuator member to heat the same and further including means filtering the DC voltage generated by the thermocouple from the AC power supply to provide a voltage representative of the temperature of the thermocouple.

14. A guide wire as in claim 6 wherein said additional actuator member has proximal and distal extremities and wherein said additional actuator member is formed so that it has a decreasing mass in a direction extending from the proximal extremity to the distal extremity to provide a guide wire in which the bend location in the second actuator member can be adjusted by adjusting the current flow through the additional actuator member.

15. A guide wire having a distal extremity with an adjustable support characteristic comprising a core wire having proximal and distal extremities, said distal extremity having a reduced cross sectional area to provide a distal extremity which is more flexible than the proximal extremity, means forming a tip secured to the distal extremity of the core wire, a superelastic sleeve of temperature activated metal alloy coaxially disposed on the distal extremity of the core wire, said superelastic sleeve being annealed so it is relatively flexible at a temperature ranging from 20° to 40° C. and becomes progressively stiffer as temperature increases, conductive means carried by the core wire for conducting electrical energy to the superelastic sleeve for supplying heat to the sleeve and extending from the proximal extremity of the core wire to the sleeve to cause the sleeve to become stiffer to thereby increase the stiffness of the distal extremity of the guide wire whereby a guide wire is provided having a distal extremity with an adjustable support characteristic which varies from a floppy characteristic to a stiff characteristic.

16. A guide wire as in claim 15 wherein said temperature activated metal alloy is a nickel-titanium alloy.

17. A guide wire as in claim 15 wherein said means for supplying electrical energy to the superelastic sleeve consists of a layer of conductive material insulated from the core wire extending from the proximal extremity of the core wire to the sleeve and making electrical contact with the proximal extremity of the sleeve and means for establishing an electrical connection between the distal extremity of the superelastic sleeve and the core wire.

18. A guide wire for use in a medical procedure for use with a power supply comprising a core wire having proximal and distal extremities, the proximal extremity having a predetermined diameter and at least a portion of the distal extremity having reduced diameter with respect to said predetermined diameter, a coil secured to the distal extremity of the core wire, an actuator member having proximal and distal extremities disposed within the coil, electrical means carried by the core wire and connected between the proximal and distal extremities of the actuator member, said actuator member being formed so that it has a decreasing mass extending from the proximal extremity to the distal extremity, said actuator member being formed of a shape memory alloy and having a predetermined shape memory causing it to bend when electrical energy is supplied thereto, said actuator member having a decreasing mass in a direction from the proximal extremity to the distal extremity so that as electrical energy is supplied thereto the position of the bend changes.

19. A guide wire as in claim 18 wherein said actuator member is rectangular in plan.

20. A guide wire as in claim 18 wherein said actuator member is triangular in plan.

21. A guide wire as in claim 18 wherein said actuator member is formed of a ternary alloy.

22. A guide wire as in claim 21 wherein said ternary alloy is Alloy K.

* * * * *